United States Patent
Bovolenta et al.

(10) Patent No.: US 10,144,937 B2
(45) Date of Patent: *Dec. 4, 2018

(54) STABLE PRODUCTION OF LENTIVIRAL VECTORS

(71) Applicant: MolMed, S.p.A., Milan (IT)

(72) Inventors: Chiara Bovolenta, Milan (IT); Anna Stornaiuolo, Milan (IT); Paolo Rizzardi, Milan (IT); Fulvio Mavilio, Evry (FR)

(73) Assignee: MolMed, S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/226,762

(22) Filed: Aug. 2, 2016

(65) Prior Publication Data

US 2018/0002721 A1 Jan. 4, 2018

Related U.S. Application Data

(62) Division of application No. 13/819,991, filed as application No. PCT/EP2011/065090 on Sep. 1, 2011, now Pat. No. 9,441,245.

(30) Foreign Application Priority Data

Sep. 2, 2010 (EP) ..................................... 10175088

(51) Int. Cl.
| | |
|---|---|
| C12N 15/86 | (2006.01) |
| C12N 15/867 | (2006.01) |
| C07K 14/54 | (2006.01) |
| C07K 14/005 | (2006.01) |
| A61K 39/21 | (2006.01) |
| A61K 39/00 | (2006.01) |
| C07K 16/10 | (2006.01) |
| A61K 38/00 | (2006.01) |

(52) U.S. Cl.
CPC ......... *C12N 15/86* (2013.01); *C12N 15/8673* (2013.01); *A61K 38/00* (2013.01); *A61K 39/21* (2013.01); *A61K 2039/525* (2013.01); *C07K 14/005* (2013.01); *C07K 14/54* (2013.01); *C07K 16/10* (2013.01); *C12N 2710/14144* (2013.01); *C12N 2740/16052* (2013.01); *C12N 2740/16122* (2013.01); *C12N 2740/16134* (2013.01); *C12N 2750/14143* (2013.01); *C12N 2750/14352* (2013.01); *C12N 2800/40* (2013.01); *C12N 2800/50* (2013.01); *C12N 2810/6054* (2013.01)

(58) Field of Classification Search
None
See application file for complete search history.

(56) References Cited

U.S. PATENT DOCUMENTS

| | | | |
|---|---|---|---|
| 6,013,516 A | 1/2000 | Verma et al. | |
| 9,133,481 B2 | 9/2015 | Bovolenta et al. | |
| 9,441,245 B2 * | 9/2016 | Bovolenta | C12N 15/8673 |
| 2005/0003547 A1 | 1/2005 | Spencer et al. | |
| 2006/0166363 A1 | 7/2006 | Zolotukhin et al. | |
| 2006/0258006 A1 | 11/2006 | Mitrophanous et al. | |
| 2013/0164840 A1 | 6/2013 | Bovolenta et al. | |
| 2014/0248695 A1 | 9/2014 | Bovolenta et al. | |

FOREIGN PATENT DOCUMENTS

| | | |
|---|---|---|
| WO | WO 98/45462 A1 | 10/1998 |
| WO | WO 2009/104964 A1 | 8/2009 |
| WO | WO 2012/028680 A1 | 3/2012 |

OTHER PUBLICATIONS

Ansorge, S., et al., "Recent progress in lentiviral vector mass production," *Biochemical Engineering Journal* 48:362-377, Elsevier B.V., Netherlands (2009).

Berns, K.I. and Linden, R.M. "The cryptic life style of adeno-associated virus," *BioEssays* 17(3):237-245, ICSU Press, United States (1975).

Berns, K.I., et al., "Study of the Fine Structure of Adeno-Associated Virus DNA with Bacterial Restriction Endonucleases," *Journal of Virology* 16(13):712-719, American Society for Microbiology, United States (1975).

Bestor, T.H., "Gene silencing as a threat to the success of gene therapy," *The Journal of Clinical Investigation* 105(4):409-411, American Society for Clinical Investigation, United States (2000).

Broussau, S., et al., "Inducible Packaging Cells for Large-scale Production of Lentiviral Vectors in Serum-free Suspension Culture," *Molecular Therapy* 16(3):500-507, The American Society of Gene Therapy, United States (2008).

Carroli R., et al., "A Human Immunodeficiency Virus Type 1 (HIV-1)-Based Retroviral Vector System Utilizing Stable HIV-1 Packaging Cell Lines," *Journal of Virology* 68(9):6047-6051, American Society for Microbiology, United States (1994).

Cheung, A.K.M., et al., "Integration of the Adeno-Associated Virus Genome into Cellular DNA in Latently Infected Human Detroit 6 Cells," *Journal of Virology* 33(2):739-748, American Society for Microbiology, United States (1980).

(Continued)

*Primary Examiner* — Nancy J Leith
(74) *Attorney, Agent, or Firm* — Sterne, Kessler, Goldstein & Fox P.L.L.C.

(57) ABSTRACT

The present invention provides new stable packaging cell lines and producer cell lines as well as methods to obtain them, and a new method to produce lentiviral vectors using such cell lines. New methods and packaging cell lines of the invention are generated using a baculo-AAV hybrid system for stable expression of structural and regulatory lentiviral proteins, such system comprising a baculoviral backbone containing an integration cassette flanked by AAV ITR, in combination with a plasmid encoding rep protein. This system allows to obtain a stable integration of the structural and regulatory HIV-1 proteins gag/pol and rev. The system allows to obtain a first intermediate including only the structural and regulatory HIV proteins gag/pol and rev, to be used as starting point to obtain stable packaging cell lines as well as producer cell lines.

8 Claims, 7 Drawing Sheets

Specification includes a Sequence Listing.

(56) References Cited

OTHER PUBLICATIONS

Cockrell, A.S., et al., "A Trans-Lentiviral Packaging Cell Line for High-Titer Conditional Self-Inactivating HIV-1 Vectors," *Molecular Therapy* 14(2):276-284, The American Society of Gene Therapy, United States (2006).
Corbeau, P., et al., "Efficient gene transfer by a human immunodeficiency virus type 1 (HIV-1)-derived vector utilizing a stable HIV packaging cell line," *Prac Natl Acad Sci USA* 93:14070-14075, National Academy of Sciences, United States (1996).
Di Nunzio, F., et al., "Transduction of Human Hematopoietic Stem Cells by Lentiviral Vectors Pseudotyped with the RD114-TR Chimeric Envelope Glycoprotein," *Human Gene Therapy* 18:811-820, Mary Ann Liebert, Inc., United States (2007).
Dull, T., et al., "A Third-Generation Lentivirus Vector with a Conditional Packaging System," *Journal of Virology* 72(11):8463-8471, American Society for Microbiology, United States (1998).
Follenzi, A., et al., "Gene transfer by lentiviral vectors is limited by nuclear translocation and rescued by HIV-1 pol sequences," *Nature Genetics* 25:217-222, Nature America Inc., United States (2000).
Ikeda, Y., et al., "Continuous high-titer HIV-1 vector production," *Nature Biotechnology* 21:569-572, Nature Publishing Group, England (2003).
Kaul, M., et al., "Regulated Lentiviral Packaging Cell Line Devoid of Most Viral cis-Acting Sequences," *Virology* 249:167-174, Academic Press, United States (1998).
Klages, N., et al., "A Stable System for the High-Titer Production of Multiply Attenuated Lentiviral Vectors," *Molecular Therapy* 2(2):170-176, Academic Press, United States (2000).
Ni, Y., et al., "Generation of a packaging cell line for prolonged large-scale production of high-titer HIV-i-based lentiviral vector," *The Journal of Gene Medicine* 7:818-834, John Wiley & Sons, Ltd., England (2005).
Palombo, F., et al., "Site-Specific Integration in Mammalian Cells Mediated by a New Hybrid Baculovirus-Adeno-Associated Virus Vector," *Journal of Virology* 72(6):5025-5034, American Society for Microbiology, United States (1998).
Poeschla, E., et al., "Development of HIV vectors for anti-HIV gene therapy," *Proc Natl Acad Sci USA* 93:11395-11399, National Academy of Sciences, United States (1996).
Porcellini, S., et al., "Chim3 confers survival advantage to CD4+ cells upon HIV-1 infection by preventing HIV-1 DNA integration and HIV-1-induced $G_2$ cell-cycle delay," *Blood* 115(20):4021-4029, The American Society of Hematology, United States (2010).
Porcellini, S., et al., "The F12-Vif derivative Chim3 inhibits HIV-1 replication in CD4+ T lymphocytes and CD34+-derived macrophages by blocking HIV-1 DNA integration," *Blood* 113(15):3443-3452, The American Society of Hematology, United States (2009).
Recchia, A., et al., "Site-Specific Integration of Functional Transgenes into the Human Genome by Adeno/AAV Hybrid Vectors," *Molecular Therapy* 10(4):660-670, The American Society of Gene Therapy, United States (2004).
Samulski, R.J., et al., "A Recombinant Plasmid from Which an Infectious Adeno-Associated Virus Genome Can Be Excised In Vitro and Its Use to Study Viral Replication," *Journal of Virology* 61(10):3096-3101, American Society for Microbiology United States (1987).
Sandrin, V., et al., "Intracellular Trafficking of Gag and Env Proteins and Their Interactions Modulate Pseudotyping of Retroviruses," *Journal of Virology* 78(13):7153-7164, American Society for Microbiology, United States (2004).
Sandrin, V., et al., "Lentiviral vectors pseudotyped with a modified RD114 envelope glycoprotein show increased stability in sera and augmented transduction of primary lymphocytes and CD34+ cells derived from human and nonhuman primates," *Blood* 100(3):823-832, The American Society of Hematology, United States (2002).
Schambach, A. and Baum, C., "Clinical Application of Lentiviral Vectors—Concepts and Practice," *Current Gene Therapy* 8:474-482, Bentham Science Publishers Ltd., Netherlands (2008).

Sena-Esteves, M., et al., "Generation of stable retrovirus packaging cell lines after transduction with herpes simplex virus hybrid amplicon vectors," *The Journal of Gene Medicine* 4:229-239, John Wiley & Sons, Ltd., England (2002).
Smith, R.H., "Adeno-associated virus integration: virus versus vector," *Gene Therapy* 15:817-822, Nature Publishing Group, England (2008).
Srinivasakumar, N., et al., "The Effect of Viral Regulatory Protein Expression on Gene Delivery by Human Immunodeficiency Virus Type 1 Vectors Produced in Stable Packaging Cell Lines," *Journal of Virology* 71(8):5841-5848, American Society for Microbiology, United States (1997).
Throm, R.E., et al., "Efficient construction of producer cell lines for a SIN lentiviral vector for SCID-X1 gene therapy by concatemeric array transfection," *Blood* 113(21):5104-5110, The American Society of Hematology, United States (2009).
Yu, H., et al., "Inducible Human Immunodeficiency Virus Type 1 Packaging Cell Lines," *Journal of Virology* 70(7):4530-4537, American Society for Microbiology, United States (1996).
Zufferey, R., et al., "Multiply attenuated lentiviral vector achieves efficient gene delivery in vivo," *Nature Biotechnology* 15:871-875, Nature Publishing Group, England (1997).
International Search Report, dated Dec. 22, 2011, for International Application No. PCT/EP2011/065089, filed Sep. 1, 2011.
International Search Report, dated Dec. 22, 2011, for International Application No. PCT/EP2011/065090, filed Sep. 1, 2011.
Fehse, B., et al., "Selective Immunoaffinity-Based Enrichment of CD34 + Cells Transduced with Retroviral Vectors Containing an Intracytoplasmatically Truncated Version of the Human Low-Affinity Nerve Growth Factor Receptor (ΔLNGFR) Gene," *Human Gene Therapy* 8:1815-1824, Mary Ann Liebert, Inc., United States (1997).
Lawn, S.D., et al., "Cellular Compartments of Human Immunodeficiency Virus Type 1 Replication In Vivo: Determination by Presence of Virion-Associated Host Proteins and Impact of Opportunistic Infection," *Journal of Virology* 74(1): 139-145, American Society for Microbiology, United States (2000).
Ye, K., et al., "Tagging retrovirus vectors with a metal binding peptide and one-step purification by immobilized metal affinity chromatography," *Journal of Virology* 78(18): 9820-9827, American Society for Microbiology, United States (2004).
Bouard, D., et al., "Viral vectors: from virology to transgene expression," *British Journal of Pharmacology* 157:153-165, The British Pharmacological Society, United Kingdom (2009).
Kootstra, N.A. and Verma, I.M., "Gene Therapy with Viral Vectors," *Annual Review of Pharmacology and Toxicology* 43:413-439, Annual Reviews, United States (2003).
Kubo, S. and Mitani, K., "A New Hybrid System Capable of Efficient Lentiviral Vector Production and Stable Gene Transfer Mediated by a Single Helper-Dependent Adenoviral Vector," *Journal of Virology* 77:2964-2971, American Society for Microbiology, United States (2003).
Lesch, H.P., et al., "Generation of lentivirus vectors using recombinant baculoviruses," *Gene Therapy* 15:1280-1286, MacMillan Publishers Limited, England (2008).
Naumann, N., et al., "Simian immunodeficiency virus lentivector corrects human X-linked chronic granulomatous disease in the NOD/SCID mouse xenograft," *Gene Therapy* 14:1513-1524, Nature Publishing Group, England (2007).
Sinn, P.L., et al.,"Gene Therapy Progress and Prospects: Development of improved lentiviral and retroviral vectors—design, biosafety, and production," *Gene Therapy* 12:1089-1098, Nature Publishing Group, England (2005).
Smith, R.H., et al., "A Simplified Baculovirus-AAV Expression Vector System Coupled With One-step Affinity Purification Yields High-titer rAAV Stocks From Insect Cells," *Molecular Therapy* 17:1888-1896, The American Society of Gene & Cell Therapy, United States (2009).
Wang, C., "Hybrid baculovirus-adeno-associated virus vectors for prolonged transgene expression in human neural cells," *Journal of NeuroVirology* 14:563-568, Journal of NeuroVirology, United States (2008).

(56) References Cited

OTHER PUBLICATIONS

Lebkowski, J.S., et al., "Adeno-Associated Virus: a Vector System for Efficient Introduction and Integration of DNA into a Variety of Mammalian Cell Types," Molecular and Cellular Biology 8:3988-3996, American Society for Microbiology, United States (1988).

* cited by examiner

SEQUENCE LISTING

```
<160> NUMBER OF SEQ ID NOS: 27

<210> SEQ ID NO 1
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="primer"
      /organism="artificial sequences"

<400> SEQUENCE: 1
agtactggag ctttgttcct tggg                                              24

<210> SEQ ID NO 2
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 2
agtactaaat ccccaggagc tg                                                22

<210> SEQ ID NO 3
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 3
cgggctgctg gcccaccagg                                                   20

<210> SEQ ID NO 4
<211> LENGTH: 24
<212> TYPE: DNA
<213> ORGANISM: artificial sequences
<220> FEATURE:
<221> NAME/KEY: source
<222> LOCATION: 1..24
<223> OTHER INFORMATION: /mol_type="DNA"
      /note="primer"
      /organism="artificial sequences"

<400> SEQUENCE: 4
atgccggggt tttacgagat tgtg                                              24

<210> SEQ ID NO 5
<211> LENGTH: 20
<212> TYPE: DNA
```

```
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 5
cttgaggagg tcttcgtcgc                                               20

<210> SEQ ID NO 6
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 6
ccctgttact tctcccctcc c                                             21

<210> SEQ ID NO 7
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 7
tgtctccgct tcttcctgcc                                               20

<210> SEQ ID NO 8
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 8
ttaaccatag aaaagaaggg g                                             21

<210> SEQ ID NO 9
<211> LENGTH: 15
<212> TYPE: PRT
<213> ORGANISM: artificial sequence
<220> FEATURE:
<223> OTHER INFORMATION: Amino Acids 95-109 of RD114-TR

<400> SEQUENCE: 9

Gln Asn Arg Arg Gly Leu Asp Leu Leu Thr Ala Glu Gln Gly Gly
1               5                   10                  15

<210> SEQ ID NO 10
<211> LENGTH: 15
<212> TYPE: PRT
<213> ORGANISM: artificial sequence
<220> FEATURE:
```

<223> OTHER INFORMATION: Amino Acids 65-79 of RD114-TR

<400> SEQUENCE: 10

Ser Gly Ile Val Arg Asn Lys Ile Arg Thr Leu Gln Glu Glu Leu
1               5                   10                  15

<210> SEQ ID NO 11
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 11
gtagcatggc gggttaatca                                                  20

<210> SEQ ID NO 12
<211> LENGTH: 27
<212> TYPE: DNA
<213> ORGANISM: artificial sequences
<220> FEATURE:
<221> NAME/KEY: source
<222> LOCATION: 1..27
<223> OTHER INFORMATION: /mol_type="DNA"
      /note="primer"
      /organism="artificial sequences"

<400> SEQUENCE: 12
ttaactacaa ggaacccta gtgatgg                                           27

<210> SEQ ID NO 13
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="primer"
      /organism="artificial sequences"

<400> SEQUENCE: 13
gtaatacgac tcactatagg gc                                               22

<210> SEQ ID NO 14
<211> LENGTH: 19
<212> TYPE: DNA
<213> ORGANISM: artificial sequences
<220> FEATURE:
<221> NAME/KEY: source
<222> LOCATION: 1..19
<223> OTHER INFORMATION: /mol_type="DNA"
      /note="primer"
      /organism="artificial sequences"

<400> SEQUENCE: 14
agggctccgc ttaagggac                                                   19

<210> SEQ ID NO 15
<211> LENGTH: 76
<212> TYPE: DNA
<213> ORGANISM: artificial sequences
<220> FEATURE:
<221> NAME/KEY: source
<222> LOCATION: 1..76

<223> OTHER INFORMATION: /mol_type="DNA"
    /note="linker sequence"
    /organism="artificial sequences"

<400> SEQUENCE: 15
gatcgtccct taagcggagc cctatagtga gtcgtattac cagggaattc gcctcgggat    60
atcactcagc ataatg                                                    76

<210> SEQ ID NO 16
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
    /note="primer"
    /organism="artificial sequences"

<400> SEQUENCE: 16
gaccacagtg atgggcagct                                                20

<210> SEQ ID NO 17
<211> LENGTH: 26
<212> TYPE: DNA
<213> ORGANISM: artificial sequences
<220> FEATURE:
<221> NAME/KEY: source
<222> LOCATION: 1..26
<223> OTHER INFORMATION: /mol_type="DNA"
    /note="primer"
    /organism="artificial sequences"

<400> SEQUENCE: 17
gccttgtaag tcattggtct taaacg                                         26

<210> SEQ ID NO 18
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
    /note="probe"
    /organism="artificial sequences"

<400> SEQUENCE: 18
tgacccgagg caccaccgac a                                              21

<210> SEQ ID NO 19
<211> LENGTH: 27
<212> TYPE: DNA
<213> ORGANISM: artificial sequences
<220> FEATURE:
<221> NAME/KEY: source
<222> LOCATION: 1..27
<223> OTHER INFORMATION: /mol_type="DNA"
    /note="primer"
    /organism="artificial sequences"

<400> SEQUENCE: 19
aggttactcc agatgtccaa ttttagc                                        27

<210> SEQ ID NO 20
<211> LENGTH: 20
<212> TYPE: DNA
<213> ORGANISM: artificial sequences

```
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 20
gggagtgggt atcgcaagag                                              20

<210> SEQ ID NO 21
<211> LENGTH: 16
<212> TYPE: DNA
<213> ORGANISM: artificial sequences
<220> FEATURE:
<221> NAME/KEY: source
<222> LOCATION: 1..16
<223> OTHER INFORMATION: /mol_type="DNA"
      /note="probe"
      /organism="artificial sequences"

<400> SEQUENCE: 21
cagagccaac aatctt                                                  16

<210> SEQ ID NO 22
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
      /note="primer"
      /organism="artificial sequences"

<400> SEQUENCE: 22
acatcaagca gccatgcaaa t                                            21

<210> SEQ ID NO 23
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="primer"
      /organism="artificial sequences"

<400> SEQUENCE: 23
atctggcctg gtgcaatagg                                              20

<210> SEQ ID NO 24
<211> LENGTH: 31
<212> TYPE: DNA
<213> ORGANISM: artificial sequences
<220> FEATURE:
<221> NAME/KEY: source
<222> LOCATION: 1..31
<223> OTHER INFORMATION: /mol_type="DNA"
      /note="probe"
      /organism="artificial sequences"

<400> SEQUENCE: 24
catcaatgag gaagctgcag aatgggatag a                                 31

<210> SEQ ID NO 25
<211> LENGTH: 18
<212> TYPE: DNA
```

```
<213> ORGANISM: artificial sequences
<220> FEATURE:
<221> NAME/KEY: source
<222> LOCATION: 1..18
<223> OTHER INFORMATION: /mol_type="DNA"
      /note="primer"
      /organism="artificial sequences"

<400> SEQUENCE: 25
tactgacgct ctcgcacc                                              18

<210> SEQ ID NO 26
<211> LENGTH: 17
<212> TYPE: DNA
<213> ORGANISM: artificial sequences
<220> FEATURE:
<221> NAME/KEY: source
<222> LOCATION: 1..17
<223> OTHER INFORMATION: /mol_type="DNA"
      /note="primer"
      /organism="artificial sequences"

<400> SEQUENCE: 26
tctcgacgca ggactcg                                               17

<210> SEQ ID NO 27
<211> LENGTH: 20
<212> TYPE: DNA
<213> ORGANISM: artificial sequences
<220> FEATURE:
<221> NAME/KEY: source
<222> LOCATION: 1..20
<223> OTHER INFORMATION: /mol_type="DNA"
      /note="probe"
      /organism="artificial sequences"

<400> SEQUENCE: 27
atctctctcc ttctagcctc                                            20
```

STABLE PRODUCTION OF LENTIVIRAL VECTORS

CROSS-REFERENCE TO RELATED APPLICATIONS

The present application is a divisional application of U.S. application Ser. No. 13/819,991, filed Oct. 15, 2015, which is a U.S. National Phase of International Application No. PCT/EP2011/065090, filed Sep. 1, 2011, which claims the benefit of European Application No. 10175088.3, filed Sep. 2, 2010, each of which is incorporated herein by reference in its entirety.

REFERENCE TO SEQUENCE LISTING SUBMITTED ELECTRONICALLY

The content of the electronically submitted sequence listing (Name: 3340_0010002_SequenceListing_ascii.txt; Size: 7,726 bytes; and Date of Creation: Oct. 15, 2013) filed herewith is incorporated herein by reference in its entirety.

FIELD OF THE INVENTION

The present invention relates to the production of lentiviral vectors (LV) for gene therapy. More particularly, the invention relates stable lentiviral packaging cell lines and methods of manufacturing packaging cell lines using an hybrid baculo-adeno associated virus (AAV) vector for stable integration of structural and regulatory lentiviral proteins.

BACKGROUND

Since the first-ever LV phase I clinical trial against AIDS in 2001, 38 phase I-II and two phase II-111 trials exploiting HIV-based LV as gene delivery vehicles have undergone authorities' scrutiny; three of them are still under review. The largest number of trials comprises monogenic disorders, some of which with large incidence such as Cooley's anemia β-thalassemia major (4 trials). Cancer and infectious diseases, mostly HIV-1 infection, follow. Commonly, the number of patients enrolled in phase I/II trials is limited, but not that in phase III. Thus stable packaging cell lines for $2^{nd}$ (LTR-based) and $3^{rd}$ (SIN-based) LV generation are urgently needed to cope LV large scale production demand for phase III trials hopefully attainable in the future in a larger number. LV production grounded on transient protocols is indeed impractical for global application under a safety, cost and reproducibility standpoint.

An increasing body of evidence indicates that LV, the most recently developed viral integrating vectors for gene therapy, are broadly applicable to transduce either terminally differentiated or cycling cells, ideal to sustain long-term transgene expression and safer than what was initially feared. The experience accumulated on Moloney murine leukemia virus (MoMLV) gamma-retroviral vectors (γRV) over the last two decades guided the fast progress on LV delivery system, whose development originated by the necessity of overcoming the inability of retrovirus to transduce non diving cells. In particular, the generation of self-inactivating (SIN) transfer vectors makes the prospect of a large use of LV in human clinical trials more feasible [1] provided the expansion and optimization of an as much efficient manufacturing process. However, in contrast to γRV, which can be produced by several human and murine commercially available packaging cell lines, LV are currently produced not only for research-grade, but also for GMP-grade, almost exclusively by transient transfection. This technology is expensive, difficult to standardize and scale-up and requires numerous downstream validation tests. Furthermore, the risk of replication competent lentivirus (RCL), possibly arising through recombination between viral sequences in the packaging and transfer vector constructs, is a rare, but more likely event during transient than stable production.

The development of a retroviral-equivalent stable packaging cell line for LV turned out to be slower and more difficult because, as opposite to gamma retrovirus, the expression of lentiviral proteins, such as the env, protease, and some accessory proteins is toxic for human cells. To overcome this problem the accessory genes, present in the very early versions of packaging cells, were later removed in the latest generations. First generation SIV- and HIV-based LV packaging cell lines were obtained from either monkey Vero, or human COS, HeLa and HEK293 adherent cells [2-5], engineered with lentivirus genomes carrying few crucial modifications such as the removal of the packaging signal. The gp120 env and most accessory genes were in fact maintained. The resulting LV titer was very low [2-5], and more importantly the possible application of these vectors was necessarily restricted to CD4$^+$ T cells for anti-AIDS gene therapy approaches. Later, gp120 env was substituted with the glycoprotein derived from the vesicular stomatitis virus (VSV-G) and all accessory genes were removed because proven dispensable for an efficient LV production. To prevent the toxicity also described for VSV-G, its expression was conditionally induced by a variety of different systems, such as the Tet, ecdysone, rev and the combination of Tet and cumate [20]. Similarly, to reduce the toxic effect of the viral protease during clone selection, the conditional expression of the gag-pol gene by the Tet and the combination of doxycycline and cumate drugs have been described [7]. In all these systems gag-pol, rev and env genes were integrated by transient transfection of plasmid DNA, followed by drug selection and cell cloning.

One of the crucial issue for the implementation of a truly stable packaging cell line is the choice of the best viral gene delivery vehicles. Most researchers integrated the gag-pol, rev and env genes by transient transfection of plasmid DNA, followed by drug selection and cell cloning [7-10]. This technology is known to suffer over time from gene silencing and gene loss [11], which can both jeopardize the long-term stability of the packaging clone.

Alternative gene delivery vehicles have been disclosed particularly in STAR [12] and in the more recently developed GPRG-TL-20 [6] packaging cell lines where the gag, pol, and rev genes were integrated into HEK293T cells by MLV-shuttle vectors. Two copies of the recoded gag-pol gene were stably integrated in STAR, whereas no such information is available for GPRG-TL-20 [6]. As opposite to STAR, where the env gene were transfected, in GPRG-TL-20 all the remaining viral genes were introduced by SIN-MLV.

Several systems exist that allow stable integration of foreign genome into host cells. Palombo et al., 1998 [13] disclose an hybrid baculovirus-AAV vector for specific integration into host cells. Such vector appears to be very effective if it includes rep gene in the same hybrid baculovirus-AAV vector. There is no mention in this reference of the construct of the present invention let alone the suggestion of using this kind of system for LV production.

Over the last almost two decades, several attempts to generate stable LV packaging cell lines have been made.

Despite the different technology disclosed, as of today none of these packaging cell lines is employed in clinical trials or corners the market yet. Therefore there is a need of new systems for large scale production of LV that are effective in terms of production capability and are safe, cost effective and reproducible.

SUMMARY OF THE INVENTION

The present invention is related to the field of production of LV. Several gene therapy clinical trials are ongoing employing LV as gene delivery vehicles. In all these trials LV production is still based on transient protocols.

The present invention provides a new strategy to generate an HIV-1-based packaging cell line. Such strategy is based on the use of a hybrid vector comprising baculoviral backbone containing an integration cassette flanked by AAV ITRs, the so-called baculo-AAV hybrid system, in combination with a plasmid encoding a rep protein. This system allows to obtain a stable integration of structural HIV-1 proteins gag/pol and rev. The system of the present invention includes a) a baculo-AAV hybrid vector characterized in that it contains two expression cassettes, one encoding lentiviral gag and pol genes and the other lentiviral rev and a selection marker, and b) a plasmid encoding a rep protein. The proposed system represents a new and advantageous way to deliver structural and regulatory HIV-1 proteins in order to stably and effectively engineer host cells with such lentiviral proteins. Using this system, it was obtained a first intermediate including only structural and regulatory HIV-1 proteins gag/pol and rev, to be used as starting point to obtain $2^{nd}$ and $3^{rd}$ generation packaging cell lines including respectively the regulatory protein (tat) and the envelope protein of interest or only the envelope protein, as well as producer cell lines including also the transfer vector.

The first intermediate carries two copies of the recombinant baculo-AAV packaging construct expressing the HIV-1 gag-pol and rev genes in a tri-cistronic configuration. Such intermediate has been called PK-7 and is referred to as PK-7 in the examples. Genome integration of baculo-AAV packaging vector was facilitated by the transient expression of the AAV rep78 protein known to be necessary for an ITR-mediated AAV vector integration [14]. Such first intermediate showed to have a surprising genetic stability for 1 year of culture that has proven the continuous production of functional LV after transient transfection of the remaining genetic elements. In addition, no silencing phenomenon have been observed in such cells. Furthermore, by exactly mapping the integration site of the two tandemly integrated packaging AAV vectors in a non-coding intergenic transcriptionally active region, we have provided a safety argument against the possible activation of dangerous genes whose mRNA can be incorporated in the LV and eventually in the host target cells.

From the first intermediate, $2^{nd}$ and $3^{rd}$ generation stable packaging cell lines can be obtained. Particularly, according to the present invention, $3^{rd}$ generation packaging cell line can be obtained by stably integrating in the first intermediate PK-7 the envelope protein of interest such as MLV 4070 env, RD114 env or GALV env retrovirus or derivatives thereof. Stable integration can be obtained using SIN-LV delivery but other gene delivery vehicles can be used. We obtained the relevant packaging cell line referred to in the example PK-7-RD, by integrating the chimeric envelope protein RD114-TR that contains the extracellular and transmembrane domain of the envelope derived from the feline endogenous retrovirus and the cytoplasmic tail of the MLV 4070 env [15]. RD114-TR chimeric envelope protein integration was obtained by SIN-LV delivery.

In order to obtain the $2^{nd}$ and $3^{rd}$ generation producer cell lines the SIN-Tat, SIN-Env and transfer vector or only the SIN-Env and transfer vector, respectively, were integrated by sequential delivery. Conceptually, the integration of one vector at the time, although time-consuming, reduces the risk of homologous recombination and thereby RCL formation.

The developed packaging system based on the use of an hybrid baculo-AAV vector for stable expression of lentiviral gag-pol and rev has been called "MolPack", therefore, $2^{nd}$ generation producer cell line developed with this system and containing RD114-TR and tat as envelope and regulatory protein, respectively, and a transfer vector encoding Chim3 as the therapeutic gene is referred to in the examples as RD2-MolPack-Chim3.

Remarkably, the titer of LV derived from RD2-MolPack-Chim3 clones is more than 2-logs higher than that of LV produced from HEK293T control cells, indicating that RD2-MolPack-Chim3 generates more functional LV compared to equivalent LV produced by transient protocol with the further advantage of the production by a stable producer cell line that is cost effective and safer.

STATEMENTS OF THE INVENTION

According to a first aspect of the invention there is provided a system for stable expression of lentiviral structural and regulatory proteins consisting of:
  i. an hybrid vector comprising baculoviral backbone containing an integration cassette flanked by AAV ITRs including two expression cassettes, wherein the first expression cassette encodes lentiviral gag and pol genes and the second one lentiviral rev and a selection marker and
  ii. an expression plasmid containing the AAV Rep Open Reading Frame (ORF) under control of a promoter.

Preferably the two expression cassettes of the hybrid vector are tail-to-tail oriented and each one is driven by a constitutive promoter and a poly A, preferably the promoter is selected from, CMV CMV IE, PGK, SV40, eF1α SFFV and RSV more preferably the promoter is a CMV IE promoter.

According to a preferred aspect of the invention the selection marker is selected from hygromycin, kanamycin, neomycin, or zeomycin resistance genes, more preferably the selection marker is hygromycin resistance gene.

Preferably the selection marker is cloned downstream an internal ribosome entry site (IRES).

Preferably the AAV rep protein is selected from rep78 or rep68. More preferably rep protein is rep78. According to another aspect of the invention, there is provided a semi-stable lentiviral packaging cell line consisting of a cell stably expressing lentiviral gag pol and rev characterized in that such cells contains stably integrated into its genome at least one copy of an integration cassette flanked by AAV ITRs including two expression cassettes, wherein the first expression cassette encodes lentiviral gag and pol genes and the second one lentiviral rev and a selection marker.

Preferably the cell is a human cell line preferably selected from HEK293, HEK293-T, HEK293-SF, TE671, HT1080 or HeLa, more preferably the cell line is HEK293-T.

Preferably the two expression cassettes are tail-to-tail oriented and each one is driven by a constitutive promoter and a poly A; preferably the promoter is selected from CMV, CMV IE, PGK, SV40, eF1α, SFFV and RSV, more preferably the constitutive promoter is a CMV IE promoter.

According to a preferred aspect of the invention the selection marker is selected from hygromycin, kanamycin, neomycin, zeomycin resistance genes; preferably the selection marker is hygromycin resistance gene. More preferably the selection marker is cloned downstream an IRES.

Preferably the AAV rep protein is selected from rep78 or rep68. More preferably rep protein is rep78. According to another aspect of the invention there is provided a method to obtain a stable lentiviral packaging cell line comprising:
i. preparing an hybrid vector (A) comprising baculoviral backbone containing an integration cassette flanked by AAVITRs including two expression cassettes, wherein the first expression cassette encodes lentiviral gag and pol genes and the second one lentiviral rev and a selection marker, and
ii. preparing an expression plasmid (B) containing the AAV rep ORF under control of a promoter
iii. transfecting cells with the expression plasmid B and subsequently infecting the cell with hybrid vector A
iv. culturing the cells in the presence of antibiotic for selection
v. obtaining cells stably expressing gag, pol and rev proteins
vi. integrating an env gene in such cells
vii. culturing the cells to obtain a cell line stably expressing gag, pol, rev and env proteins According to another aspect of the invention there is provided a method to obtain a stable lentiviral packaging cell line comprising:
i. preparing an hybrid vector (A) comprising baculoviral backbone containing an integration cassette flanked by AAVITRs including two expression cassettes, wherein the first expression cassette encodes lentiviral gag and pol genes and the second one lentiviral rev and a selection marker, and
ii. preparing an expression plasmid (B) containing the AAV rep ORF under control of a promoter
iii. transfecting a cell with the expression plasmid B and subsequently infecting the cell with hybrid vector A
iv. culturing the cells in the presence of antibiotic for selection
v. obtaining cells stably expressing gag, pol and rev proteins
vi. integrating a lentiviral tat gene in such cells
vii. culturing the cells to obtain a cell line stably expressing gag, pol, rev and tat proteins
viii. integrating an env gene in such cells
ix. culturing the cells to obtain a cell line stably expressing gag, pol, rev, tat and env protein Preferably the two expression cassettes of the hybrid vector are tail-to-tail oriented and each one is driven by a constitutive promoter and a poly A, preferably the promoter is selected from CMV, CMV IE, PGK, SV40, eF1α, SFFV, and RSV, more preferably the constitutive promoter is a CMV IE promoter.

Preferably the tat gene is HIV-1 tat.

According to a preferred aspect of the invention the selection marker is selected from hygromycin, kanamycin, neomycin, zeomycin resistance gene; preferably the selection marker is hygromycin resistance gene, more preferably the selection marker is cloned downstream an IRES.

Preferably the env gene is integrated in host cells using AAV vector, retroviral vector, stable plasmid integration or homologous recombination. According to a more preferred aspect the env gene is integrated using a SIN lentiviral vector.

Preferably the env gene is selected from MLV 4070 env, RD114 env, chimeric envelope protein RD114-TR, chimeric envelope protein RD114-pro baculovirus GP64 env or GALV env or derivatives thereof; more preferably the env gene is the gene encoding the chimeric envelope protein RD114-TR.

In a preferred embodiment there is provided a SIN lentiviral vector comprising an expression cassette containing from 5' to 3' end a CMV promoter the β-globin intron containing an RRE element in its sequence and the RD114-TR ORF, for the stable integration of the chimeric envelope protein RD114-TR.

Preferably the AAV rep protein is selected from rep78 or rep68. More preferably rep protein is rep78.

According to another aspect of the invention there is provided a stable lentiviral packaging cell line containing stably integrated into its genome:
i. at least one copy of an integration cassette flanked by AAV ITRs including two expression cassettes, wherein the first expression cassette encodes lentiviral gag and pol genes and the second one lentiviral rev and a selection marker
ii. at least one copy of env According to the same aspect of the invention the above stable lentiviral packaging cell line further comprises at least one copy of HIV-1-tat gene stably integrated into its genome.

Preferably the cell is a human cell line, preferably the cell line is selected from HEK293, HEK293-SF, HEK293-T, TE671, HT1080 or HeLa, more preferably the cell line is HEK293-T.

Preferably, the two expression cassettes of the integration cassette are tail-to-tail oriented and each one is driven by a constitutive promoter and a poly A, preferably the promoter is selected from CMV, CMV IE, PGK, SV40, eF1α, SFFV and RSV, more preferably the constitutive promoter is a CMV IE promoter.

According to a preferred aspect of the invention the selection marker is selected from hygromycin, kanamycin, neomycin, zeomycin resistance gene; preferably the selection marker is hygromycin more preferably the selection marker is cloned downstream an IRES.

Preferably the env gene is integrated in host cells using AAV vector, retroviral vector, stable plasmid integration or homologous recombination. According to a more preferred aspect the env gene is integrated using a SIN lentiviral vector.

Preferably the env gene is selected from MLV 4070 env, RD114 env, the chimeric envelope protein RD114-TR, the chimeric envelope protein RD114-pro, baculovirus GP64 env or GALV env or derivatives thereof more preferably the env gene is the gene encoding the chimeric envelope protein RD114-TR.

According to another aspect there is provided a method for producing lentiviral vectors comprising:
i. culturing a stable lentiviral packaging cell line containing stably integrated into its genome at least one copy of an integration cassette flanked by AAV ITRs including two expression cassettes, wherein the first expression cassette encodes lentiviral gag and pol genes and the second one lentiviral rev and a selection marker; and at least one copy of env
ii. Inserting in the stable packaging cell line a transfer vector Preferably the two expression cassettes are tail-to-tail oriented and each one is driven by a constitutive promoter and a poly A; preferably the promoter is selected from CMV, CMV IE, PGK, SV40, eF1α, SFFV and RSV, more preferably the constitutive promoter is a CMV IE promoter.

Preferably the selection marker is selected from hygromycin, kanamycin, neomycin, zeomycin resistance gene; more preferably the selection marker is hygromycin resistance gene. More preferably the selection marker is cloned downstream an IRES.

Preferably the env gene is selected from VSV-G env, MLV 4070 env, RD114 env, chimeric envelope protein RD114-TR, chimeric envelope protein RD114pro, baculovirus GP64 env or GALV env or derivatives thereof, more preferably the env gene is the gene encoding the RD114-TR.

According to another aspect of the present invention there is provided a producer cell line containing stably integrated into its genome:
i. at least one copy of an integration cassette flanked by AAVITRs including two expression cassettes, wherein the first expression cassette encodes lentiviral gag and pol genes and the second one lentiviral rev and a selection marker
ii. at least one copy of env gene
iii. a transfer vector According to the same aspect of the present invention the above producer cell line further contains lentiviral tat gene stably integrated into its genome.

Preferably the cell is a human cell line preferably selected from HEK293, HEK293-T, HEK293-SF, TE671, HT1080 or HeLa, more preferably the cell line is HEK293-T.

Preferably the two expression cassettes of the integration cassette are tail-to-tail oriented and each one is driven by a constitutive promoter and a poly A, preferably the promoter is selected from CMV, CMV IE, PGK, SV40, eF1α, SFFV and RSV, preferably the constitutive promoter is a CMV IE promoter.

According to a preferred aspect of the invention the selection marker is selected from hygromycin, kanamycin, neomycin, zeomycin resistance gene; more preferably the selection marker is hygromycin more preferably the selection marker is cloned downstream an IRES.

Preferably the env gene is integrated in host cells using AAV vector, retroviral vector, stable plasmid integration or homologous recombination. According to a more preferred aspect the env gene is integrated using a SIN lentiviral vector.

Preferably the env gene is selected from MLV 4070 env, RD114 env, the chimeric envelope protein RD114-TR, the chimeric envelope protein RD114-pro, baculovirus GP64 env or GALV env or derivatives thereof, more preferably the env gene is the gene encoding the chimeric envelope protein RD114-TR.

According to another aspect there is provided a method for producing lentiviral vectors comprising culturing a producer cell line containing stably integrated into its genome:
i. at least one copy of an integration cassette flanked by AAV ITRs including two expression cassettes, wherein the first expression cassette encodes lentiviral gag and pol genes and the second one lentiviral rev and a selection marker;
ii. at least one copy of env
iii. at least one copy of a transfer vector encoding the gene of interest Preferably the two expression cassettes are tail-to-tail oriented and each one is driven by a constitutive promoter and a poly A; preferably the promoter is selected from CMV, CMV IE, PGK, SV40, eF1α, SFFV and RSV, more preferably the constitutive promoter is a CMV IE promoter.

Preferably the selection marker is selected from hygromycin, kanamycin, neomycin, zeomycin resistance gene; more preferably the selection marker is hygromycin resistance gene. More preferably the selection marker is cloned downstream an IRES.

Preferably the env gene is selected from VSV-G env, MLV 4070 env, RD114 env, chimeric envelope protein RD114-TR, chimeric envelope protein RD114pro, baculovirus GP64 env or GALV env or derivatives thereof, more preferably the env gene is the gene encoding the RD114-TR.

DETAILED DESCRIPTION OF THE INVENTION

A detailed description of preferred features and embodiments of the invention will be described by way of non-limiting example.

The invention can be put into practice by a person of ordinary skill in the art who will employ, unless otherwise indicated, conventional techniques of chemistry, molecular biology, microbiology, recombinant DNA and immunology. All such techniques are disclosed and explained in published literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); Current Protocols in Immunology, ch. 12, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridization: Principles and Practice; Oxford University Press; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. All these publications are incorporated by reference.

Baculo-AAV Hybrid System

The present invention provides a new strategy to generate an HIV-1-based packaging cell line. Optimization of production system for LV is one of the critical issues that needs to be solved for the development of gene therapy medicine based on LV technology. Despite the growing number of clinical trials employing this technology, LV are still produced, in such trials, using transient transfection protocols. In this way, production of LV is still very expensive and unsatisfactory for larger number of patients. For this reason, many efforts have been made to develop stable packaging cell lines for LV. One of the critical issues in the development of a stable lentiviral packaging cell line is choosing the right vehicle for engineering host cells. In many cases host cells have been engineered using plasmids, but, in such cases, genome instability and gene silencing phenomena have also been observed. Retroviral vectors have been used to stable integrate gag/pol and rev genes in two other cases. None of the stable packaging cell line developed so far has been employed in clinical trials.

The strategy of the present invention is based on the use of a system for stable expression of lentiviral structural and regulatory proteins consisting of an hybrid vector comprising a baculoviral backbone containing an integration cassette flanked by AAV ITRs including two expression cassettes, wherein the first expression cassette encodes lentiviral gag and pol genes and the second one lentiviral rev and a selection marker; together with an expression plasmid containing the AAV rep ORF under control of a promoter. The presence of baculoviral backbone allows to host a big and complex integration cassette including two expression cassettes encoding several different proteins. The resulting baculo-AAV packaging vector allows to engineer host cells with gag pol and rev proteins that are necessary to stably and effectively produce LV, through only one infection event.

Genome integration of baculo-AAV packaging vector was obtained by the transient expression of the AAV rep protein. This system allowed to obtain integration of AAV vectors in a non-coding intergenic transcriptionally active region, thus excluding activation of dangerous genes whose mRNA can be incorporated in the LV and eventually in the host target cells.

The proposed system represents a new and advantageous way to deliver structural HIV-1 proteins in order to stably and effectively engineer host cell with structural and regulatory lentiviral proteins. In a preferred embodiment, the two expression cassettes included in the baculo-AAV packaging construct are tail-to-tail oriented and each one is driven by a constitutive promoter and a poly A, preferably the promoter is selected from, CMV, CMV IE, PGK, SV40, eF1α, SFFV, and RSV, more preferably the promoter is a CMV IE promoter. According to a preferred aspect of the invention the selection marker included in the AAV packaging is selected from hygromycin, kanamycin, neomycin, zeomycin resistance genes; preferably the marker is hygromycin resistance gene, more preferably the selection marker is cloned downstream an IRES.

Genome integration of baculo-AAV packaging vector was obtained by the transient expression of AAV rep protein for an ITR-mediated AAV vector integration. In a preferred embodiment rep protein is selected from rep78 and rep68, more preferably the protein is rep78.

Using this system, it was possible to obtain cells engineered to stably express HIV-1 proteins gag/pol and rev that we called semi-stable packaging cell line. Particularly, the present invention discloses and claims such engineered cells and their use to obtain $2^{nd}$ and $3^{rd}$ generation packaging cell lines including structural and regulatory proteins and the envelope protein of interest, and producer cell line including also the transfer vector, as well as method to produce stable packaging cell lines.

Semi-Stable Packaging Cell Line

Semi-stable packaging cell line of the present invention consists of host cells carrying at least one copy of the recombinant baculo-AAV packaging construct expressing the HIV-1 gag-pol and rev genes. Genome integration of baculo-AAV packaging vector has been obtained by the transient expression of the AAV rep protein in order to obtain ITR-mediated AAV vector integration. Preferably the two expression cassettes are tail-to-tail oriented and each one is driven by a constitutive promoter and a poly A preferably the promoter is selected from CMV, CMV IE, PGK, SV40, eF1α, SFFV and RSV. More preferably the constitutive promoter is a CMV IE promoter.

According to a preferred aspect of the invention the selection marker is selected from hygromycin, kanamycin, neomycin, zeomycin resistance gene; preferably the selection marker is hygromycin resistance gene, more preferably the selection marker is cloned downstream an IRES.

Preferably the AAV rep protein is selected from rep78 and rep68. More preferably rep protein is rep78. Host cell lines that can be engineered to obtain the semi-stable packaging cell line are human cell lines selected from HEK293, HEK293-T, HEK293-SF, TE671, HT1080 or HeLa, more preferably the cell line is HEK293-T.

Such semi-stable packaging cell line is suitable for the output of a potentially large variety of LV, with different env and different transfer vectors in a semi-stable production system. Therefore, it represents a great advantage for a more effective production of lentiviral vectors since it allows costs reduction, it does not require using the GMP-grade plasmid DNA encoding gag-pol and rev, and the risk of RCL formation secondary to recombination events between the plasmids during transient transfection is reduced.

Semi-stable packaging cell line of the present invention showed to have a surprising genetic stability for 1 year of culture that has proven the continuous production of functional LV after transient transfection of the remaining genetic elements. In addition, no silencing phenomena have been observed in fact, both titer and infectivity of lentiviral particles obtained using this intermediate remained unaffected after 1 year. Such data were confirmed both in the presence or absence of selective pressure. Remarkably, no comparable data regarding the integration stability of an AAV-ITR mediated cassette are available in the literature. The only related information is that a human bone marrow derived, fibroblast-like cell line (Ruddle's Detroit 6 cells) infected with wild type AAV serotype 2 (AVV-2) maintained viral sequences in a latent state for at least 47 and 118 passages [16,17]. As shown in the examples the semi-stable packaging cell line of the present invention survived for at least 102 passages.

Stable Packaging Cell Line

The present invention provides a method to obtain a stable lentiviral packaging cell line. Such method is based on the use of a baculo-AAV packaging construct for stable integration of at least one copy of an integration cassette containing two expression cassettes, one encoding lentiviral gag and pol genes and the second one lentiviral rev and a selection marker. Stable integration of this cassette is obtained by co-expression of a rep protein that allows ITR mediated stable integration in host cell. The so engineered host cell is then cultured in the presence of antibiotic and then cloned. The obtained semi-stable packaging cell line is the starting point for the generation of $2^{nd}$ or $3^{rd}$ generation lentiviral packaging cell line. Particularly, $3^{rd}$ generation stable packaging cell line is obtained by further integrating desired env protein. $2^{nd}$ generation stable packaging cell line is obtained by first integrating HIV-1 Tat protein and then the desired envelope.

Envelope protein and HIV-1 tat can be stably integrated in host cells using AAV vector, retroviral vector, stable plasmid integration or homologous recombination. Preferably envelope proteins and HIV-1 tat are integrated in host cell using an HIV-SIN vector. Several kinds of envelope protein can be used such as MLV 4070 env, RD114 env, the chimeric envelope protein RD114-TR, the chimeric envelope protein RD114-pro, baculovirus GP64 env or GALV env or derivatives thereof. More preferably the env gene is the gene encoding the chimeric envelope protein RD114-TR.

In order to obtain stable integration of RD114-TR envelope protein, it was initially developed a SIN construct containing the BamHI-BamHI fragment derived from the pCMV-RD114-TR plasmid carrying the RD114-TR ORF under the control of the CMV promoter. This construct did not generate RD114-TR protein. An unexpected finding during the construction of the SIN-RD114-TR LV was realizing that the β-globin intron must be necessarily included between the CMV promoter and the RD114-TR ORF. In general, the majority of the cellular and viral gene expression cassettes hedged in a SIN-LV context are devoid of intron elements because of the risk of splicing between the SD of the vector and the SA of the intron and the consequent excision of the promoter contained in the expression cassette. To circumvent this pitfall, a new SIN-LV carrying two RRE elements was generated, one in the canonical SIN-LV configuration between the SD and SA sequences and one within the β-globin intron.

Based on these findings, it was argued that the unexpected requirement of the β-globin intron to obtain RD114-TR production may reflect the presence of instability or negative sequences in the RD114-TR ORF or in the 328-bp fragment encompassing the region from the RD114-TR stop codon and the 3'BamHI restriction enzyme site present in the SIN-RD114-TR construct. GeneOptimizer® Assisted Sequence analysis performed by GENEART AG (Regensburg, Germany) determined that codons with a bad codon usage were spread all over the RD114-TR gene and the 328-bp fragment, giving reason of our assumption. Furthermore, codon optimization analysis indicated that the codon adaptation index (CAI) improved from 0.65 to 0.98 (where a CAI of 1 is the optimum). Therefore, in principle, an alternative and simpler approach to integrate RD114-TR into RD-MolPack using either MLV-based or HIV-based SIN vectors could be to use recoded RD114-TR. Thus constructs containing codon optimized sequences have been prepared and tested. On the contrary, it was found that codon optimization allows RD114-TR precursor protein (PR) translation, even in the absence of the β-globin intron, but, unexpectedly, the high level of PR is not processed by furin in the due SU and TM subunits. Therefore, RD114-TR has been successfully integrated in the packaging cell line using an HIV-based SIN vector including the β-globin intron in the construct between the CMV promoter and the RD114-TR ORF. In a preferred embodiment there is provided a SIN-LV comprising an expression cassette containing from 5' to 3' end a CMV promoter the β-globin intron containing an RRE element in its sequence and the RD114-TR ORF.

The present invention provides a method for producing LV comprising:
i. Culturing a stable packaging cell line as described above
ii. Inserting in the semi-stable packaging cell line a transfer vector The production of LV currently employed in clinical trials is still based on transient transfection of all required proteins. On the contrary, the methods and the packaging cell lines of the present invention allows for a stable production. Particularly, the baculo-AAV hybrid expression system used in the method of the present invention, advantageously allows a stable and safe introduction of structural (gag/pol) and regulatory (rev) HIV-1 proteins, in only one transfection/infection and cloning round. The intermediate obtained with such expression system is stable, does not show silencing phenomena and allows to develop $2^{nd}$ and $3^{rd}$ generation packaging cell lines that are a very important tools for development of fast and effective protocols for LV production. The stable packaging cell lines of the present invention can be used for a cost effective and safer production. In fact, the total absence of transfection allows for cost reduction and reduces the possibility of recombination events, potentially leading to the formation of RCL. Moreover it has been found that stable packaging cell lines obtained with the method of the invention are able to produce LV with a titer at least comparable or even higher than LV produced with transient protocols.

Producer Cell Line

Producer cell line can be achieved by stably integrating transfer vector encoding the gene of interest (GOI) into a stable packaging cell line as described above. The present invention further provides a method for producing LV comprising culturing such producer cell line.

Remarkably the average titer and infectivity of LV produced from $2^{nd}$ generation stable packaging cell line referred to in the example as RD2-MolPack-Chim3 clones is more than 2-logs higher than that of LV produced from HEK293T control cells, indicating that RD2-MolPack-Chim3 generates LV more functional compared to equivalent LV produced by transient protocol. Of interest is the clone RD2-MolPack-Chim3.14, which spontaneously grows in suspension and produces LVs with a titer of $1.0 \times 10^6$ TU/ml on SupT1 cells and of $0.5 \times 10^6$ TU/ml in CD34$^+$ HSCs.

EXAMPLES

Example I: General Methods

Plasmids

Figure 1:
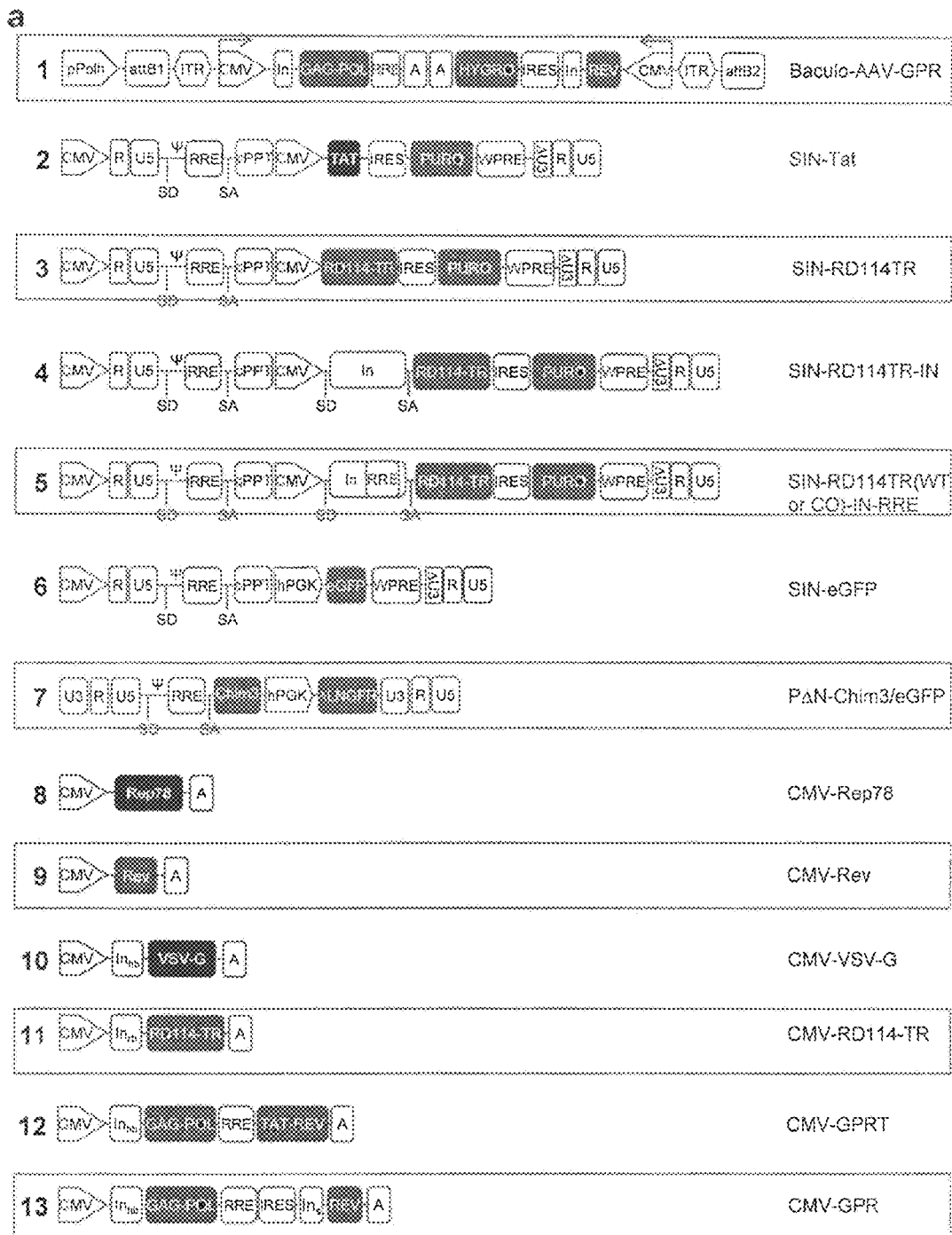
FIG. 1 Schemes of RD-MolPack development. (a) Schematic representation of the DNA plasmids used in the study. pPolh, polyhedrin promoter; attB1, attachment B1; ITR, inverted terminal repeat; CMV, cytomegalovirus promoter; In, intron; RRE, rev responsive element; A, polyA sequence; IRES, internal ribosome entry site; SD, splice donor; SA, splice acceptor; Ψ, packaging signal; WPRE, woodchuck hepatitis post-transcriptional regulatory element; cPPT, central polypurine tract; hPGK, human posphoglycerate kinase promoter. (b) Cartoon of the Rep78-mediated genomic integration of the AAV-GPR vector. AAV Rep78 promotes the excision of the ITR-flanked AAV-GPR cassette and facilitates its integration into human chromosomes. (c) Flow chart of the development strategy of either $2^{nd}$- or $3^{rd}$-generation RD-MolPack stable packaging cell lines.
Figure 1:
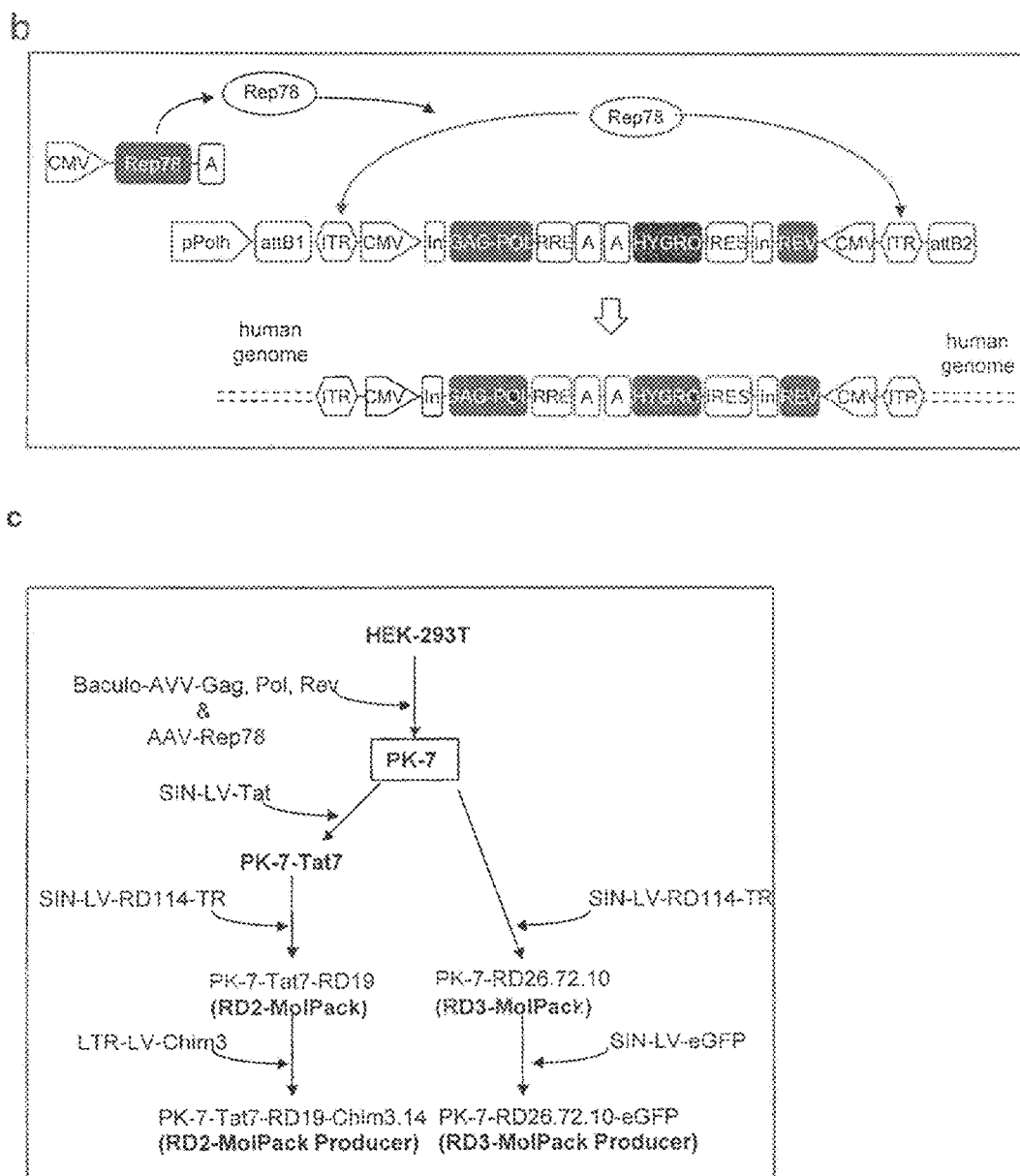

Wild-type HIV-1 gag, pol and rev genes were excised by MluI/NarI and MluI/NotI digestions from the pCG719-pKLgagpol (hereafter named CMV-GPR for simplicity) (FIG. 1a, scheme 13) and pCG720-pKrev (CMV-Rev) (FIG. 1a, scheme 9) plasmids, respectively [27]. The viral genes were inserted into the Gateway® pENTR™4 shuttle vector (Invitrogen, Co., Carlsbad, Calif.) in two distinct expression cassettes tail-to-tail oriented, each cassette driven by a CMV IE promoter and carrying a polyA sequence. The first cassette expresses the gag and pol genes whereas the second one the rev gene and the selection marker hygromycin resistance (hygro) gene; hygro was cloned downstream an IRES to allow bi-cistronic translation. The two expression units were introduced into the XbaI site of the recombinant pSUB201 plasmid carrying an infectious AAV genome [18]. The resulting 5'ITR-CMV-GagPol-polyA-polyA-hygro-IRES-Rev-CMV-ITR3' cassette was then excised and inserted into the GatewaypENTR™4 shuttle vector. The recombinant hybrid baculo-AAV packaging vector (Baculo-AAV-GPR) (FIG. 1a, scheme 1) was obtained by means of the bacteriophage lambda site-specific recombination system between the pENTR™ 4 shuttle entry vector, containing the two cassettes, and the BaculoDirect Linear DNA (BaculoDirect™ Baculovirus Expression Systems, Invitrogen, Co.). During homologous recombination the polyhedrin gene of the baculo DNA was thereby replaced with the GPR double cassette. The pABCMV-Rep78 expression plasmid (CMV-AAV-Rep78) was obtained by cloning the AAV-rep78 ORF under the CMV IE promoter of the expression vector pABS.43 as described in Recchia et al., 2004 [19] (FIG. 1a, scheme 8). The pMD.G plasmid (CMV-VSV-G) [20], encodes the vesicular stomatitis envelope glycoprotein (VSV-G) (FIG. 1a, scheme 10). The $3^{rd}$ generation transfer vector, pCCLsin.PPT.hPGK.eGFP.WPRE.Amp (SIN-eGFP) [21] expresses the eGFP gene under the constitutive promoter hPGK (FIG. 1a, scheme 6). The 2nd-generation PΔN-Chim3 transfer vector expressing the anti-HIV-1 Chim3 transgene was described in Porcellini et al., 2009 & 2010 [23,24] (FIG. 1a, scheme 7). The SIN-RD114-TR vectors (FIG. 1a, schemes 3-5) were constructed following different strategies by using the RD114-TR ORF excised from the pCMV-RD114-TR (CMV-RD114-TR) (FIG. 1a, scheme 11) plasmid, which encodes the chimeric RD114-TR envelope, made of the extracellular and trans-membrane domains of the feline endogenous retrovirus RD114 envelope and the cytoplasmic tail (TR) of the A-MLVenv 4070A [22]. Briefly, the CMV-RD114-TR, CMV-RD114-TR-IN and CMV-RD114-TR-IN-RRE cassettes were each cloned into the MluI site of the SIN-polyMluI vector, a modified version of the SIN-eGFP vector in which the hPGK-eGFP cassette was removed and substituted with the EcoRV-MluI-SmaI-MluI-NotI-SacI-BglII-BamHI-SalI polylinker. The SIN-RD114-TR-IN and the RD114-TR-IN-RRE constructs (FIG. 1a, scheme 4 and 5, respectively) contain the rabbit β-globin intron present in the CMV-RD114-TR vector (FIG. 1a, scheme 11). In the SIN-RD114-TR-IN-RRE, the 230-bp RRE element, PCR amplified as described in the "PCR analysis" section, was integrated into the ScaI site of the β-globin intron element. The 2d-generation packaging pCMV-ΔR8.74 (CMV-GPRT) construct (FIG. 1a, scheme 12) encoding the HIV-1 gag, pol, rev and tat genes [25]. The SIN-Tat vector (FIG. 1a, scheme 2) was constructed by inserting the tat gene, derived from the CMV-GPRT plasmid (FIG. 1a, scheme 12), into the EcoRI site of the pIRESpuro3 (Clontech Laboratories Inc., a TakaraBio Company, Mountain View, Calif.) and then by cloning the bi-cistronic CMV-Tat-IRES-puro cassette into the MluI of the SIN-polyMluI vector.

Cells

Spodoptera frugiperda (Sf9) insect cells (Invitrogen, Co.) were grown in suspension in TC-100 medium (Invitrogen, Co.) supplemented with 10% FCS (EuroClone Ltd, UK) and a combination of penicillin-streptomycin and glutamine (PSG) at 27° C. in the absence of $CO_2$. Human embryo kidney 293T (HEK293T) cells and its derivative clones (PK-7 and PK-7 derivatives) were propagated in Dulbecco's Modified Eagle Medium (DMEM) supplemented with 10% FCS and PSG. CEM A3.01 and SupT1 T cells were grown in RPMI 1640 supplemented with 10% FCS and PSG. $CD34^+$ haemopoietic stem cells (HSC) and neonatal leukocytes were purified from umbilical cord blood (UCB) centrifugation on a Ficoll-Hypaque gradient (Lymphoprep, Nycomed Pharma AS, Oslo, Norway). After gradient separation, $CD34^+$ HSC were isolated from the collected UCB mononucleated cell ring by positive selection using CD34 MicroBeads Kit and MiniMACS Separator Columns (Miltenyi Biotec, Sunnyvale, Calif.). $CD34^+$ cells purity (>92%) was established by FACS analysis (FACSCalibur BD Bioscience, San Jose, Calif.) and the FlowJo software (Tree Star, Inc., Ashland, Oreg.), using the anti-CD34-PE Ab (BD Pharmingen™, San Diego, Calif.). $CD34^+$ cells were pre-stimulated for 24 hours in 20% serum Iscove's Modified Dulbecco's Medium (IMDM) containing human stem cell factor (h-SCF) 100 ng/ml (R&D Systems, Minneapolis, Minn.), h-Flt3L 100 ng/ml (Peprotech, Rocky Hill, N.J.), h-IL-6 20 ng/ml (R&D Systems) and human thrombopoietin (h-Tpo) 20 ng/ml (Peprotech) and maintained in the same medium during transduction. Neonatal leukocytes were stimulated for 48 hours with the soluble anti-human CD3 (30 ng/ml) (Orthoclone OKT3, Janssen-Cilag, UK) and recombinant human IL-2 (rhIL-2) 50 U/ml (Chiron, Emeryville, Calif.) in RPMI and then kept in RPMI supplemented with 10% FCS, PSG, and rhIL-2.

The RD2-MolPack-Chim3.14 clone was adapted to grow in Dulbecco's Medium (DMEM) containing 2.5% FCS as follows: the cells were grown in 125-ml shake flasks on a rotary shaker at 120 rpm at 37° C. in a 5% CO2 humidified air atmosphere, to a density of $1.5×10^6$ cells/ml. The viability was maintained ≥70%, cells were split at $0.5×10^6$ cells/ml, and the medium was changed daily. Over multiple passages the FCS was decreased from 10% to 5% to 2.5%; each serum change was performed after at least two culture passages.

Baculovirus Production and Baculo-GPR Infection of HEK293T Cells

Baculovirus, carrying the recombinant hybrid Baculo-AAV-GPR DNA genome, was produced following the BaculoDirect method using the Gateway® adapted Baculovirus DNA system (Invitrogen, Co.). Recombinant Baculovirus titer was evaluated by plaque assay and corresponded to $1×10^{11}$ pfu/ml after three passages of viral amplification in Sf9 cells. PK-7 clone was obtained by transfecting $1.5×10^6$ HEK293T cells with 4 μg of AAV-rep78 expression plasmid and 24 hours afterwards infected with the recombinant Baculo-AAV-GPR at an MOI of 1,000. Cells were maintained without hygromycin for 4 days and then $5×10^5$ cells were seeded in 22 10-cm dishes in the presence of hygromycin (100 μg/ml) at serially diluted concentrations. The 22 dishes were screened for p24gag production by ELISA. Only one dish, in which cells were seeded at $3.7×10^4$ cells/dish, released sufficient p24gag in the supernatant. The dish contained 40 colonies which were all picked-up and screened. Three of them, scoring positive for p24Gag production, were further characterized.

LV Production and Titration

Pseudo-typed LV produced from HEK293T cells were obtained by transient co-transfection of the following plasmids: the packaging constructs CMV-GPR ($3^{rd}$-generation) [or CMV-GPRT ($2^{nd}$-generation)], the VSV-G or RD114-TR envelope constructs, and the $3^{rd}$-generation SIN-eGFP [26] or the 2 d-generation either PΔN-Chim3 [23] or PΔN-eGFP transfer vectors. The ratio of packaging:envelope:transfer vector was 6.5:3.5:10 μg DNA unless otherwise indicated. LV from PK-7 clone were generated by co-transfecting the env-expressing plasmid and the transfer vector, whereas LVs produced from PK-7-RD and PK-7-Tat7-RD clones were obtained by transfecting only the appropriate transfer vector. Transient transfections were performed with either the standard $Ca^{++}$-phosphate method or the Fugene6™ system following the manufacturer's instruction (Roche Diagnostics Corporation, Indianapolis, Ind.) obtaining similar results. Supernatants were harvested 48 hours after transfection and filtered through a 0.45-μm filter. Titer was calculated on SupT1, CEM A3.01, primary activated peripheral blood mononucleated cells (PBMC) and umbilical cord blood derived $CD34^+$ HSC depending on the type of experiments. Briefly, SupT1 and activated primary mononucleated cells were transduced by two cycles of spinoculation (1,240×g for 1 hour) in the presence of polybrene (8 μg/ml) (Sigma-Aldrich, St Louis, Mo.) separated by an overnight resting phase; $CD34^+$ HSCs were transduced for 24 hours on retronectin-coated plates (Takara Bio, Otsu, Japan) without polybrene. Transduction efficiency was monitored by flow cytometry analysis (FACS Calibur BD Bioscience, San Jose, Calif.) of eGFP expression (SIN-eGFP) or ALNFGR expression (PΔN-Chim3), as described in Porcellini et al., 2009 & 2010 [23,24], using the FlowJo software (Tree Star, Inc., Ashland, Oreg.). Only transduction values ranging from 5 to 20% positive cells were used to calculate the titer of each LV preparation according to the following formula: TU=[number of cells×(% GFP/100)]/vol sup (in ml).

Titer-Based Clone Screening Protocol

To speed-up selection, we screened all PK-7 derivative subclones by calculating LV titer of their supernatants. We set up a $Ca^{++}$-phosphate-based one- or two-plasmid co-transfection in small scale to generate LV whose potency was then calculated on SupT1 cells by a small-scale transduction protocol. Briefly, $6×10^4$/well PK-7 derivative cells were seeded in 48-well plate and 24 hours later co-transfected with the remaining plasmids required to obtain functional LV. Forty-eight hours after transfection, 200 μl of culture supernatants were used to transduce $3×10^4$/well SupT1 cells seeded at the concentration of $7.5×10^4$/ml. The titer threshold score was imposed $≥1×10^2$ TU/ml.

Northern and Southern Blot Assays

Northern blot assay.

Total RNA was extracted by Trizol Reagent (Life Technologies™ Inc., Gaithersburg, Md.) following manufacturer's instructions. Five g/sample was run on 0.8% agarose-formaldehyde gel, transferred onto Hybond-N membrane by capillary transfer, and finally probed with 1×10⁶ dpm/ml of a ³²P-labelled 550-bp RD114-TR probe in PerfectHyb PLUS hybridization buffer (Sigma Chemical Corp., St. Louis, Mo.). After extensive washes the membranes were exposed to X-ray films at −70° C.

Southern Blot Assay.

Genomic DNA (gDNA) was isolated by the QIAamp Mini kit (QIAGEN GmbH, Germany) according to manufacturer's instructions. Baculovirus DNA was extracted from viral particles by the QIAamp DNA micro kit (QIAGEN). After overnight digestion with the indicated restriction enzymes, 10 μg of gDNA was run on 0.8% agarose gel, blotted by Southern capillary transfer onto nylon membranes (Duralon, Stratagene, TX, USA) and then hybridized to 1×10⁶ dpm/ml of ³²P-random primed labeled either 600-bp CMV or 11-kb GPR cassette, 250-bp tat, 600-bp Chim3, and 500-bp RD114-TR specific probe, in PerfectHyb PLUS hybridization buffer. After extensive washes the membranes were exposed to X-ray films at −70° C. or to Phosphorlmager (Molecular Dynamics, Sunnyvale, Calif.).

Analytical PCR Analysis

The 230-bp RRE amplicon was obtained by using 1 ng SIN-eGFP vector as DNA template and the set of primers: RRE-forward: 5'-AGT ACT GGA GCT TTG TTC CTT GGG-3' (SEQ ID NO:1); RRE-reverse: 5'-AGT ACT AAA TCC CCA GGA GCT G-3' (SEQ ID NO:2) at the following PCR conditions: 98° C. for 7 minutes, 30 cycles of 94° C. for 30 seconds, 50° C. for 30 seconds, and 72° C. for 30 seconds.

PCR analysis for screening of residual integration of the AAV-Rep78 plasmid into PK-7 cells was performed on 300 ng of genomic gDNAs using the set of primers: AAV-Rep78 forward: 5'-CGG GCT GCT GGC CCA CCA GG-3' (SEQ ID NO:3); AAV-Rep78 reverse: 5'-ATG CCG GGG TTT TAC GAG ATT GTG-3' (SEQ ID NO:4) and the following PCR conditions: 98° C. for 7 minutes, 30 cycles of 94° C. for 30 seconds, 66° C. for 30 seconds, and 72° C. for 1.5 minutes.

C. for 30 seconds, 52° C. for 30 seconds, and 72° C. for 1.5 minutes.

p24gag ELISA

Physical LV production was measured in culture supernatants by the Alliance HIV-1 p24 Antigen ELISA kit (Perkin Elmer Life and Analytical Sciences, Inc. Waltham, Mass.) following manufacturer's instructions, with the assumption that 1 pg p24gag corresponds to 1×10⁴ physical particles.

Western Blot Analysis

Whole-cell and nuclear extracts derived from PK-7 cells and viral proteins derived from isolated cell-free VLP or LV were prepared as previously described [23,24]. Proteins were size-fractionated by SDS-PAGE, and electroblotted to Hybond ECL nitrocellulose membranes (GE Healthcare, Life Sciences, UK Ltd, UK). Membranes were blocked in 5% low-fat dry milk, and then incubated with the appropriate primary Ab. The anti-HIV-1 serum, obtained from an AIDS patient, was used at 1:2,000 dilution; the anti-RD114-TR rabbit serum [22], recognizing two 15-mer peptides (aa 95-109, QNRRGLDLLTAEQGG (SEQ ID NO: 9) and aa 65-79, SGIVRNKIRTLQEEL (SEQ ID NO:10)) in the ectodomain of the protein, at 1:500 dilution; the HIV-1 rev MoAb (Rev-6, sc-69730) and the affinity purified rabbit polyclonal anti-YY1 Ab (C-20, sc-281) (S. Cruz Biotechnology, Inc., S. Cruz, Calif.) and the mouse anti-p24gag (Acris Antibodies, Germany) at 1:200, 1:1,000 and 1:500 dilution, respectively. Ab binding was visualized by the enhanced chemiluminescence system ECL (ECL, Amersham) following manufactures's instructions.

Vector Copy Number (VCN) Quantification by Real-Time TaqMan PCR

The vector copy number (VCN) of the integrated vector was established by quantitative TaqMan PCR using an ABI Prism 7,900 FAST instrument (Applied Biosystems, Foster City, Calif.) and analyzed by SDS 2.3 software (Applied Biosystems). PCR conditions were the following: 2 minutes at 50° C. and 5 minutes at 95° C., followed by 40 cycles of 15 seconds at 95° C. and 15 seconds at 60° C., with an increment of 0.1° C./cycle for GAG target sequence. gDNA was amplified by using the following primers and probes:

| Target | Name | Sequence |
|---|---|---|
| Chim3 | NGRF for | 5'-GAC CAC AG TGA TGG GCA GCT-3' (SEQ ID NO: 16) |
|  | NGFR-rev exo | 5'-GCC TTG TAA GTC ATT GGT CTT AAA CG-3' (SEQ ID NO: 17) |
|  | NGFR | FAM 5'-TGA CCC GAG GCA CCA CCG ACA-3' TAMRA (SEQ ID NO: 18) |
| RD114-TR | RD for | 5'-AGG TTA CTC CAG ATG TCC AAT TTT AGC-3' (SEQ ID NO: 19) |
|  | RD rev | 5'-GGG AGT GGG TAT CGC AAG AG-3' (SEQ ID NO: 20) |
|  | RD114tr | FAM 5'-CAG AGC CAA CAA TCT T-3' MGB (SEQ ID NO: 21) |
| GAG | NA2 GAG for | 5'-ACA TCA AGC AGC CAT GCA AAT-3' (SEQ ID NO: 22) |
|  | NA2 GAG rev | 5'-ATC TGG CCT GGT GCA ATA GG-3' (SEQ ID NO: 23) |
|  | GAG | FAM 5'-CAT CAA TGA GGA AGC TGC AGA ATG GGA TAG A-3' TAMRA (SEQ ID NO: 24) |
| Tat (HIV LTR) | HIV for | 5'-TACTGACGCTCTCGCACC-3' (SEQ ID NO: 25) |
|  | HIV rev | 5'-TCTCGACGCAGGACTCG-3' (SEQ ID NO: 26) |
|  | HIV | FAM-5'-ATCTCTCTCCTTCTAGCCTC-3' MGB (SEQ ID NO: 27) |

To establish the orientation of the two GPR cassettes, PCR amplification was performed on 300 ng gDNAs using the set of primers: rev forward: 5'-CTT GAG GAG GTC TTC GTC GC-3' (SEQ ID NO:5); beta-globin reverse: 5'-CCC TGT TAC TTC TCC CCT TCC-3' (SEQ ID NO:6); rev forward nested: 5'-TGT CTC CGC TTC TTC CTG CC-3' (SEQ ID NO:7); beta-globin nested reverse: 5'-TTA ACC ATA GAA AAG AAG GGG-3' (SEQ ID NO:8) and the following conditions: 94° C. for 2 minutes, 35 cycles of 94°

Ligation-Mediated (LM)-PCR

Genomic DNA was extracted from PK-7 cells by QIAamp DNA Mini Kit (QIAGEN) according to the manufacturer's instructions and digested with BglII and BamHI at 37° C. overnight. Ligation of an adaptor 76-bp oligonucleotide linker compatible with the 5'-GATC-3' sticky ends was performed under standard conditions. LM-PCR was carried out using the following couple of nested primers: the ITR forward: 16s: 5'-GTA GCA TGG CGG GTT AAT CA-3' (SEQ ID NO:11), and 17s/long nested: 5'-TTA ACT ACA AGG AAC CCC TAG TGA TGG-3' (SEQ ID NO:12); the linker reverse primers: Linker-1: 5'-GTA ATA CGA CTC ACT ATA GGG C-3' (SEQ ID NO:13) and Linker-2 nested: 5'-AGG GCT CCG CTT AAG GGA C-3' (SEQ ID NO:14). The linker sequences corresponded to 5'-GAT CGT CCC TTA AGC GGA GCC CTA TAG TGA GTC GTA TTA CCA GGG AAT TCG CCT CGG GAT ATC ACT CAG CAT AAT G-3' (SEQ ID NO:15). Two rounds of LM-PCR were carried out using AmpliTaq Gold DNA Polymerase (Applied Biosystems), each comprising 30 cycles (95° C. for 30 seconds, 52° C. for 30 seconds, 72° C. for 2 minutes). PCR amplicons were cloned using the TOPO® cloning kit (Invitrogen, Co.) and plasmid colonies carrying inserts of approximately 100-200-bp were selected for sequencing. Sequence homologies were identified by BLAST search, NCBI.

Fluorescence In Situ Hybridization (FISH)

Metaphase chromosomes were obtained by treating PK-7 cells with colchicine (10 µg/ml) (Sigma # C9754) for 2 hours at 37° C. After phosphate buffer saline (PBS) washing, cells were kept in hypotonic solution (75 mM KCl) for 6 minutes at room temperature (RT), fixed with 4 washes of methanol/acetic acid (3:1) and then spread on a clean glass slide. Cytogenetic samples were denatured in 70% formamide solution for 2 minutes at 72° C., dehydrated by cold 70%, 85%, and 95% ethanol consecutive washes and then air dried. The specific probes were prepared as follows: the 13-kb plasmid DNA containing the GPR cassette was labeled using the Random Primed DNA Labeling Kit (Roche Applied Science, Indianapolis, Ind.) with SpectrumOrange™-dUTP (Vysis, Inc., Downers Grove, Ill.), whereas the control 30-kb cosmid DNA containing the human hox4 gene was labeled using the FISHBright™ Nucleic Acid Labeling kit (Kreatech Biotechnology, Amsterdam, The Netherlands). Hybridization was performed by incubating 5 ng/µl of each probe in 250 µl of 50% formamide, 2×SSC, and 10% dextran sulfate and 50 ng/µl of human $C_0T$-1 DNA hybridization buffer (Invitrogen). Samples were coated with denatured probes for 10 minutes at 75° C., covered with Parafilm® M, and incubated overnight at 37° C. in a moist chamber. Samples were washed once in 0.4×SSC, pH=7 at 72° C. for 2 minutes, once in 4×SSC, pH=7 containing 0.0025% Tween-20 for 30 seconds at RT and twice in PBS 1× for 1 minute at RT. Slides were counterstained with 0.02 µg/µl of 49,6-diamidino-2-phenylindole (DAPI) (Sigma). Visualization and photographic images were taken with a Nikon 80i upright microscope (Nikon Instruments S.p.A., Italy) using the green (FITC) and spectrum orange (spectrum orange) filter illumination. Images were processed with Genikon software (Nikon).

Example II: Generation of the First Intermediate PK-7 Clone

Figure 5:
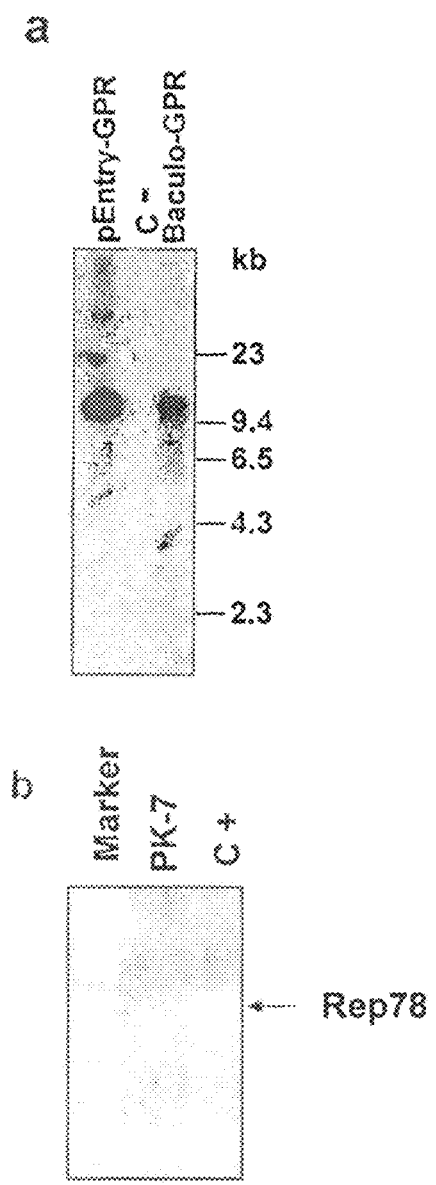
FIG. 5 Analysis of Baculo-AAV-GPR genomic DNA and of Rep78 putative residual DNA integration. (a) Southern blot analysis of the recombinant baculovirus-AAV DNA. DNA was extracted from baculovirus particles, digested overnight with MluI restriction enzyme and, after blotting, probed with the 11-kb GPR cassette specific probe. Entry-GPR plasmid (1 pg) and baculovirus empty DNA (100 ng) were loaded as positive and negative control, respectively. (b) Detection of putative residual rep78 plasmid DNA integration into PK-7 cells. Rep78 specific PCR was carried out using the PK-7 genomic DNA as sample template and the CMV-Rep78 (1 pg) plasmid as positive control.

To obtain the RD-MolPack packaging cell line for the continuous production of either $2^{nd}$- or $3^{rd}$-generation LV, several HEK293T-derived intermediate clones were developed. The first one was named PK-7 and was obtained by stable integration of HIV-1 gag, pol, and rev genes by means of the recombinant hybrid baculo-AAV vector (rhBaculo-AAV-GPR) (FIG. 1a, scheme 1). This delivery system exploits the integrase activity of AAV-rep78 protein, provided transiently, to excise and integrate the AAV ITR-flanked integration cassettes into human chromosomes (FIG. 1b). The rh-baculo-AAV vector was generated by homologous recombination between the BaculoDirect Linear DNA and the Gateway® pENTR™4 entry plasmid containing the ITR-flanked GPR cassettes (FIG. 1a, scheme 1). After 3 cycles (p3) of recombinant baculovirus amplification in Sf9 insect cells, the titer and the potential recombination events of the hybrid baculo-AAV DNA were checked by plaque assay and viral genomic DNA Southern blot, respectively. The titer at p3 corresponded to $6 \times 10^{10}$ pfu/ml, and Southern blot analysis revealed a single sharp band, demonstrating no recombination events during the virus amplification process (FIG. 5).

Figure 2:
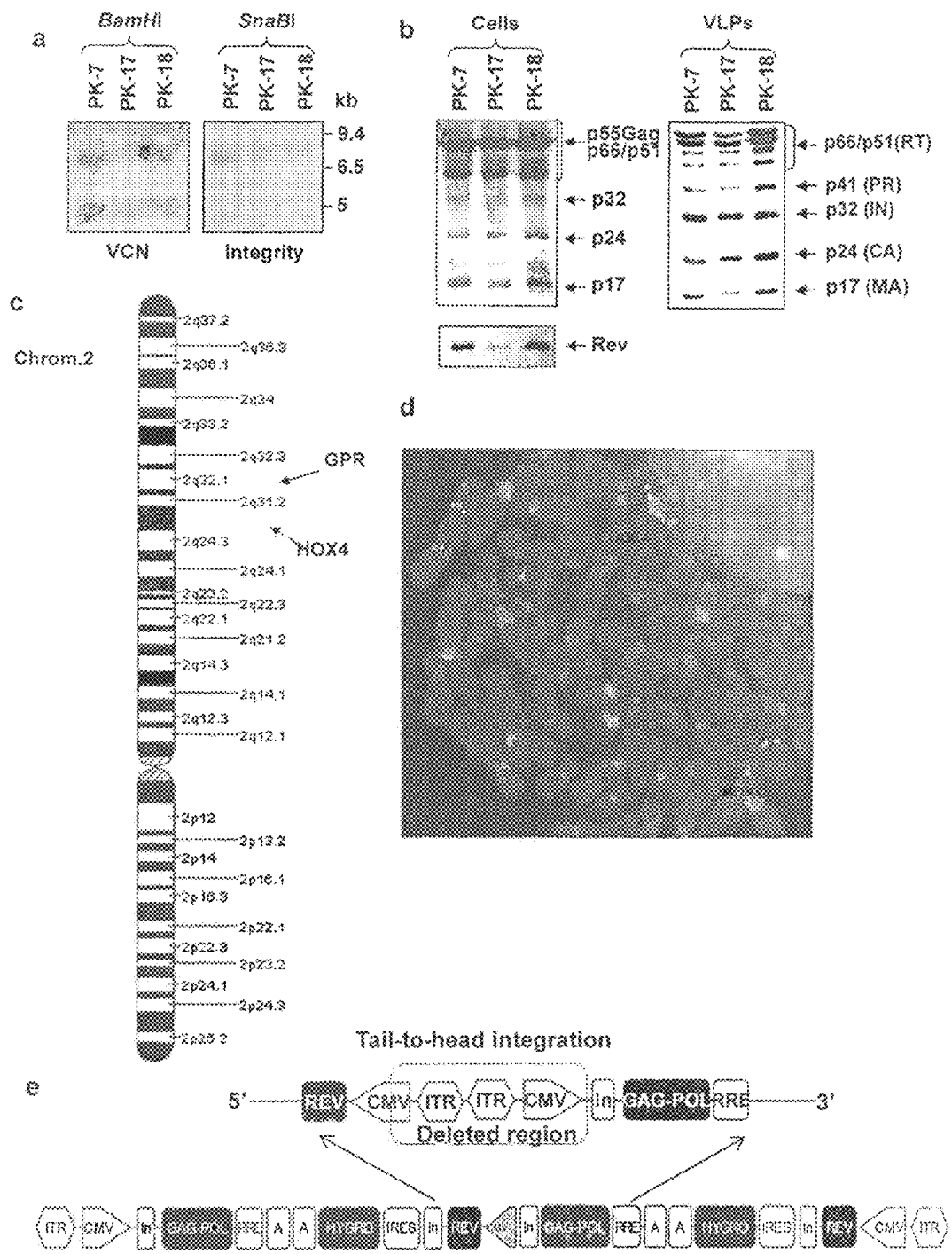
FIG. 2 Characterization of the PK clones. (a) Southern blot analysis of the AAV-GPR vector integration. To establish the number of copies and the integrity of the cassette, genomic DNA (10 μg) derived from PK clones was digested with two different restriction enzymes, BamHI and SnaBI, respectively. (b) Western blot analysis of the viral proteins produced from the GPR cassette. Left panel, cell extracts (50 μg/lane) obtained from the PK clones were hybridized to an anti-HIV-1 human serum recognizing HIV-1 proteins. The membrane was sequentially hybridized with an anti-rev specific Ab. Right panel, 30 ng p24Gag-equivalent of viral like particles (VLP) produced from PK clones were processed identically to the cellular extracts. (c) Schematic mapping of the GPR-cassette integration by LM-PCR technique which identified the DNA break-point in the long arm of chromosome 2 at the 2q32.1 location. (d) Co-localization of the AAV-GPR cassette and the human Hox4 gene into chromosome 2. In situ hybridization of PK-7 metaphase chromosomes was carried out using a gag-specific (red) and a Hox4-specific (green) probe, respectively. (e) Schematic representation of the rearrangement of the two GPR integrated cassettes in the PK-7 clone and their tail-to-head orientation.

Next, the dose and time of AAV-Rep78 plasmid transfection and of rh-baculo-AAV infection and the cloning conditions of infected HEK293T cells were carefully defined (FIG. 1c). In fact, the choice of these experimental settings turned out to be critical. Thus after testing a wide-range of conditions, it was eventually established that a single dose of AAV-rep78 plasmid DNA transfected 24 hours before rh-baculo-AAV infection at the MOI of 1,000 corresponded to the best experimental design. Moreover, it was observed that seeding a total of $5 \times 10^5$ cells distributed in 22 90 mm-Petri dishes, each dish seeded at different concentration and adding hygromycin 100 µg/ml after 4 days from seeding was the best condition to collect the largest number of cell clones. Only three of the 360 counted clones, PK-7, PK-17 and PK-18, expressed p24Gag above the 100 pg/ml settled threshold. Southern blot analysis of the clones revealed that each clone contains two copies of the correct-in-size vector (FIG. 2a). To exclude possible integration of residual AAV-Rep78 plasmid DNA, rep78 specific PCR was carried out on PK-7 gDNA detecting no positive signal (FIG. 5b). The HIV-1 protein expression pattern expressed from the GPR cassette was monitored by Western blot of the three PK clones and their matching viral like particles (VLP) released in the medium. All viral proteins were properly processed, correct-in-size and in the right, relative proportion (FIG. 2b). The future working PK clone was selected by calculating on SupT1 cells the potency of the LV produced from the three clones after being co-transfected with the VSV-G plasmid and the $3^{rd}$-generation transfer vector SIN-eGFP (Table 1). Of note, although the titer of control HEK293T LV produced by transient transfection was 5-fold higher than that of PK-7 and PK-18 LV, its infectivity was almost identical to that of the PK LV, suggesting that the PK clones generate LV that under a "quality" standpoint are comparable to those produced by conventional methods (Table 1). Although the potency of PK-7 and PK-18 LV was similar, PK-7 clone was selected for further genetic manipulation because its morphology, growth, viability and p24Gag production values scored better than those of PK-18 clone (Table 1).

TABLE 1

Potency of VSV-G pseudotyped LV produced from PK clones

| Clones | Titer (TU/ml)[a] |
|---|---|
| PK-7[b] | $1.1 \times 10^7$ |
| PK-17 | $5.4 \times 10^6$ |
| PK-18 | $1.0 \times 10^7$ |
| HEK-293T | $5.8 \times 10^7$ |
| | p24Gag (ng/ml) |
| PK-7 | 406 |
| PK-17 | 636 |
| PK-18 | 326 |
| HEK-293T | 1694 |
| | Infectivity (TU/ng p24Gag) |
| PK-7 | $2.7 \times 10^4$ |
| PK-17 | $8.4 \times 10^3$ |

TABLE 1-continued

Potency of VSV-G pseudotyped LV produced from PK clones

| Clones | |
|---|---|
| PK-18 | $3.0 \times 10^4$ |
| HEK-293T | $3.4 \times 10^4$ |

[a]Titer was calculated on SupT1 cells 3 days after transduction. Cells were transfected with the VSV-G and SIN-eGFP plasmids.
[b]Bold indicates the selected clone.

Next, the integration of the ITR-flanked GPR cassette in PK-7 clone was characterized in depth by quantitative LM-PCR, TaqMan PCR (FIG. 2c) and FISH techniques (FIG. 2d). To exactly map the integration site, LM-PCR studies were carried out, which spotlighted the breakpoint at the chromosome 2, 2q32.1 (FIG. 2c). This result was confirmed by in situ hybridization with the specific GPR probe which revealed a single spot into chromosome 2 based on the arm length and centromere position (FIG. 2d). To confirm this location assignment, it was used the Hox4 probe, which is known to map into chromosome 2q31.2. As HEK293T cells are triploid, Hox4 was rightly detected in all three chromosomes 2 (FIG. 2d). Lastly, it was confirmed by quantitative TaqMan PCR that two copies were integrated and by nested PCR with an appropriate design of the primers (FIG. 2e) that the two copies were in tandem orientation, tail-to-head. Tail-to-head orientation is the natural configuration observed also for the integration of wild type AAV and most rAAV vector concatamers into the host cell genome [17]. Sequence analysis of the amplicon encompassing the tail-to-head junction revealed that a 910-bp fragment comprising 303-bp of the 3' CMV promoter of the first cassette together with both ITRs of the first and second cassette and the entire 5' CMV promoter of the second cassette were lost (FIG. 2e, red box). The majority of the vector-cellular recombination events occurs in fact within the ITR sequences of the vector. This rearrangement has caused in the PK-7 cells the lack of transcription of the gag-pol gene of the second cassette and likely the lack of transcription of the rev and hygro genes of the first cassette. However, it is worth mentioning that the 285-bp region left of the deleted CMV promoter (FIG. 2e, gray triangle in the center of the scheme) still contains the TATA box that might be sufficient to drive transcription of the rev and hygro genes. In conclusion, PK-7 contains two integrated cassettes, which collectively transcribe one gag-pol gene and one or two rev and hygro genes.

To demonstrate the stability of PK-7 clone over time, the cells were cultivated in the presence or absence of hygromycin for 350 days, corresponding to ca 420 cell doublings, and measured p24Gag production on a per cell basis (Table 2). The average production in the presence of hygromycin corresponds to $15.34 \pm 8.47$SD ng p24Gag/$1 \times 10^6$ cells, whereas in the absence of antibiotic is $6.70 \pm 3.51$SD ng p24Gag/$1 \times 10^6$ cells (Table 2).

TABLE 2

Stability of PK-7 clone over time

| Passage | Hygromycin p24Gag ng/$10^{6a}$ | No Hygromycin p24Gag ng/$10^{6a}$ |
|---|---|---|
| P2 | 10.00 | 8.10 |
| P6 | 7.00 | 4.80 |
| P10 | 11.40 | 4.00 |
| P16 | 5.00 | 4.80 |
| P20 | 0.30 | 5.20 |
| P24 | 7.20 | 6.50 |
| P28 | 9.20 | 4.40 |
| P32 | 6.20 | 8.80 |
| P36 | 11.00 | 9.60 |
| P40 | 18.00 | 10.00 |
| P44 | 4.30 | 8.40 |
| P48 | 37.50 | 3.80 |
| P52 | 7.00 | 3.20 |
| P56 | 11.00 | 6.70 |
| P60 | 19.00 | 4.40 |
| P64 | 22.00 | 18.70 |
| P68 | 15.20 | 8.00 |
| P72 | 16.50 | 4.90 |
| P76 | 17.80 | 7.60 |
| P80 | 30.00 | 11.00 |
| P84 | 27.00 | 8.40 |
| P88 | 23.20 | 3.50 |
| P92 | 23.00 | 7.50 |
| P98 | 16.70 | 1.36 |
| P102 | 19.00 | 3.85 |
| Mean ± SD | 15.34 ± 8.47 | 6.70 ± 3.51 |
| | Titer (TU/ml)[b] | |
| P60 | $3.2 \times 10^6$ | $2.0 \times 10^6$ |
| P102 | $2.7 \times 10^6$ | $1.3 \times 10^6$ |
| | p24Gag (ng/ml)[b] | |
| P60 | 86 | 38 |
| P102 | 80 | 13 |
| | Infectivity (TU/ng p24Gag)[b] | |
| P60 | $4.2 \times 10^4$ | $5.2 \times 10^4$ |
| P102 | $3.3 \times 10^4$ | $1.0 \times 10^5$ |

[a]p24Gag level expressed as ng/1 × $10^6$ cells
[b]Potency values of VSV-G pseudotyped LV produced after transfection of PK-7 cells with SIN-eGFP and VSV-G plasmids and tested on SupT1 cells 3 days after transduction This difference likely derives from the fact that hygromycin drug pressure keeps on an "on" state the transcription of the hygro resistance gene and thereby the chromatin as well. This might favour the higher transcription of the gag-pol genes. To evaluate whether the VLP generated from PK-7 clone were functional even after hundreds of doublings, PK-7 cells were co-transfected at p60 and p102 with VSV-G envelope and SIN-eGFP transfer vector and the LV potency was calculated on SupT1 cells. Remarkably, the titer and infectivity of LV produced both in the presence and absence of the selection drug persisted to normal level still after such prolonged time (Table 1). These data demonstrate no genetic instability of the GPR cassette regardless the presence or absence of drug pressure and allowed us to avoid the use of hygromycin in future characterization. No comparable data regarding the integration stability of an AAV-ITR mediated cassette are available in the literature. The only related information is that a human bone marrow derived, fibroblast-like cell line (Ruddle's Detroit 6 cells) infected with wild type AAV serotype 2 (AVV-2) maintained viral sequences in a latent state for at least 47 passages and 118 passages [16,17]. Remarkably, PK-7 cells survived for at least 102 passages.

Figure 3:
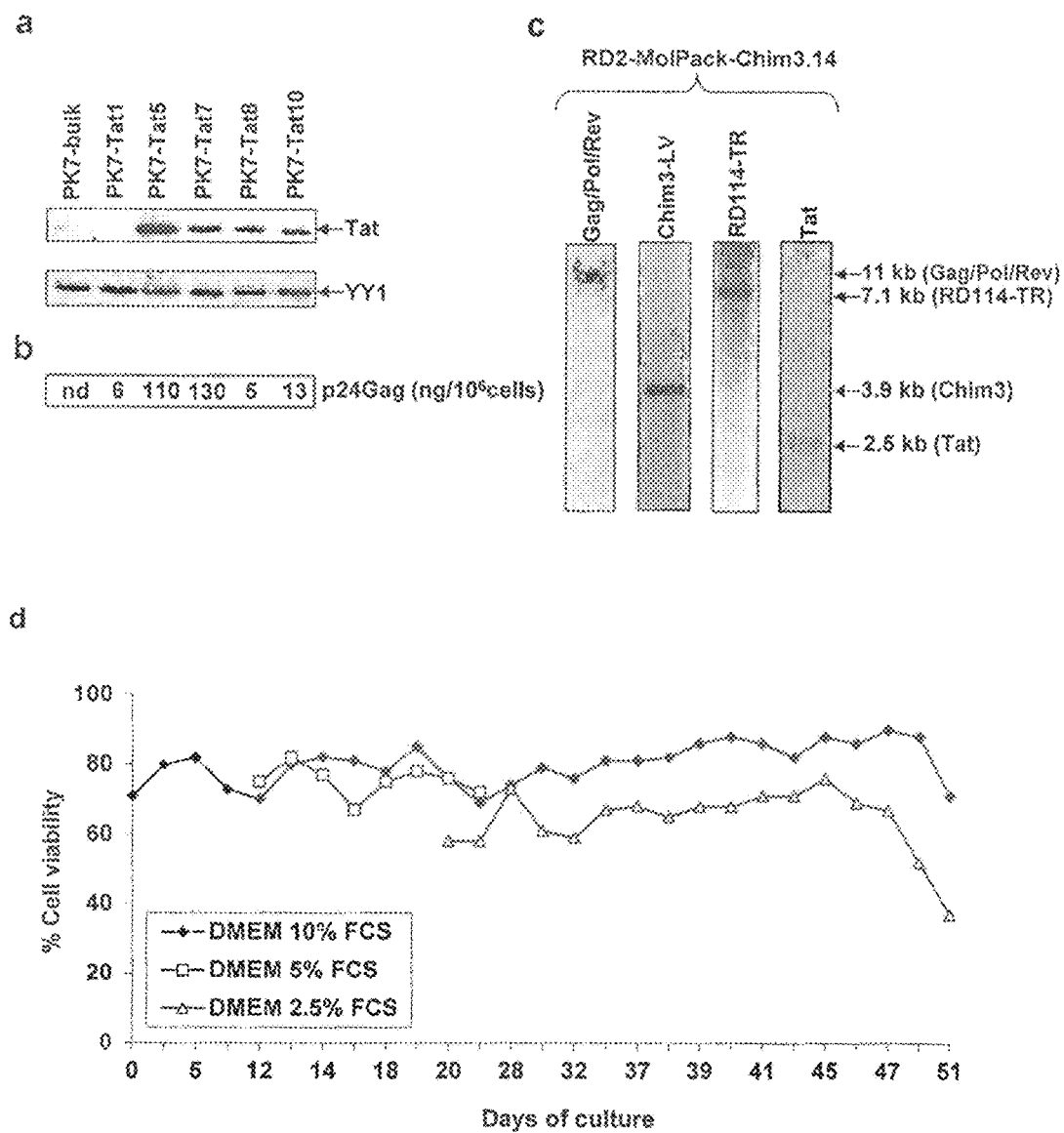
FIG. 3 Expression of Tat in PK-7-Tat clones. (a) Western blot analysis of nuclear extracts (50 μg/lane) obtained from PK-7-Tat bulk cells and five derived clones. The membrane was hybridized with the anti-tat specific Ab and, after stripping, with the anti-YY1 Ab, that detects the constitutive nuclear transcription factor, YY1 as internal control. (b) Production of p24 gag expressed on a per cell basis from the selected clones was measured by ELISA. (c) Southern blot analysis of the genomic DNA of RD2-MolPack-Chim3.14 for the integrity of the SIN-LV-Tat, SIN-LV-RD114-TR and LTR-LV-Chim3 vectors. The vector copies number of the three vectors calculated by TaqMan PCR is indicated into brackets. (d) Graph of the cell viability of RD2-MolPack-Chim3.14 cells cultivated in different % of FCS as indicated in the legend for almost two months.

Example III: Development of the Second Intermediate, PK-7-Tat7 Clone for $2^{nd}$ Generation RD2-MolPack The next step towards the development of the $2^{nd}$ generation RD-MolPack (FIG. 1c) consisted in the stable integration of the HIV-1 regulatory factor Tat into PK-7 cells by means of SIN-LV delivery (FIG. 1, scheme 2). Cells were transduced by two cycles of spinoculation and then cloned by limiting dilution after puromycin selection. 11 growing clones were picked up and, after a first screening based on p24gag production, Tat expression was established by Western blot using nuclear extracts obtained from five clones showing ≥5 ng p24gag/1×10$^6$ cells values. Only PK-7-Tat5 and PK-7-Tat7 clones displayed high level of tat (FIG. 3a) and p24gag (FIG. 3b). Thus only these two clones were further characterized establishing by TaqMan PCR that PK-7-Tat5 contains 12 and PK-7-Tat7 six tat gene copies; LV potency was also measured by co-transfecting the remaining VSV-G envelope plasmid and the PΔN-eGFP 2$^{nd}$-generation transfer vector. Although the titer of both clones was 2-log lower, the infectivity was only 1-log lower than control cells (Table 3). On this basis, PK-7-Tat7 was selected as the intermediate clone on which subsequently integrate the RD114-TR envelope.

TABLE 3

Potency of VSV-G pseudotyped LV produced from PK7-Tat clones

| Clones | Titer (TU/ml)$^a$ |
|---|---|
| PK-7-Tat5 | $1.5 \times 10^5$ |
| PK-7-Tat7$^b$ | $1.6 \times 10^5$ |
| PK-7 | $1.0 \times 10^7$ |
| HEK-293T | $1.4 \times 10^7$ |
| | p24Gag (ng/ml) |
| PK-7-Tat5 | 67.5 |
| PK-7-Tat7 | 48 |
| PK-7 | 120 |
| HEK-293T | 163 |
| | Infectivity (TU/ng p24Gag) |
| PK-7-Tat5 | $2.2 \times 10^3$ |
| PK-7-Tat7 | $3.4 \times 10^3$ |
| PK-7 | $8.3 \times 10^4$ |
| HEK-293T | $8.5 \times 10^4$ |

$^a$Titer was calculated on SupT1 cells 3 days after transduction. PK-7 cells were transfected with the VSV-G and PΔN-eGFP plasmids, whereas HEK-293T cells with the VSV-G, CMV-GPRT and PΔN-eGFP plasmids.
$^b$Bold indicates the selected clone.

Example IV: Construction of the SIN-RD114-TR-IN-RRE Vector

Figure 4:
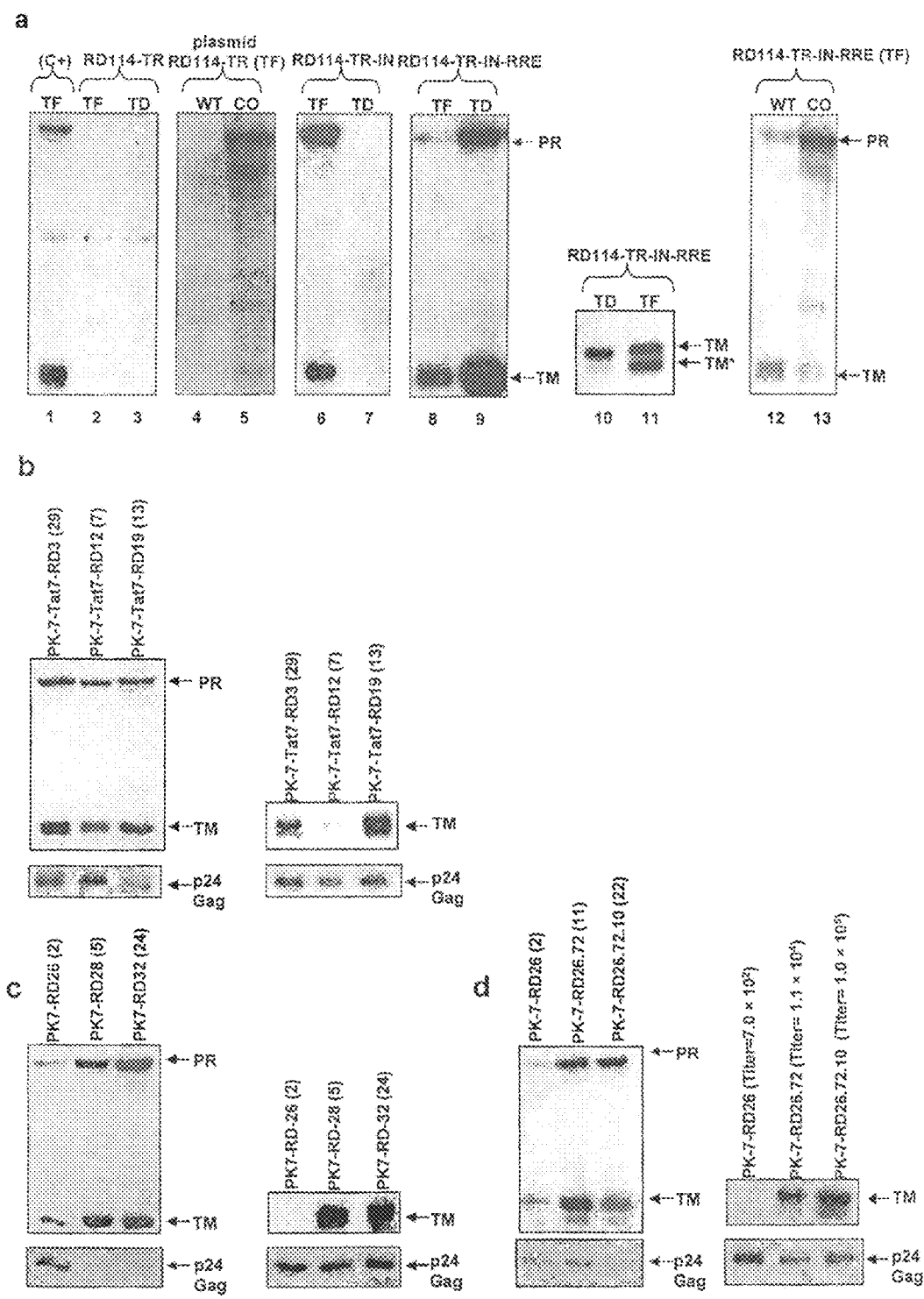
FIG. 4 Analysis of RD114-TR envelope expression. (a) Western blot assay to detect RD114-TR expression from different constructs. PK-7 cells were transiently transfected (TF) with the CMV-RD114-TR plasmid (lane 1) and the corresponding whole cell extract was used as positive control. SIN-RD114-TR (lanes 2 and 3), pIRES-RD114-TR-WT and pIRES-RD114-TR-codon optimized (CO) (lanes 4 and 5), SIN-RD114-TR-IN (lanes 6 and 7) SIN-RD114-TR-IN-RRE (lanes 8 and 9), SIN-RD114-WT-TR-IN-RRE and SIN-RD114-TR-CO-IN-RRE (lanes 12 and 13) were either transfected (TF) into PK-7 cells or packaged as transfer vector into VSV-G pseudotyped LV, generated by standard triple transfection of HEK293T. SIN-RD114-TR containing LV were then used to spinoculate PK-7 cells (TD). Lanes 1-9, 12 and 13 correspond to cell extracts (50 µg/lane); lanes 10 and 11 correspond to LV (30 ng p24gag-equivalent/lane). The filters were probed with an anti-RD114-TR Ab, which recognizes the precursor (PR) and the transmembrane (TM), but not the surface (SU) subunit of the chimeric envelope. The TM* band corresponds to a shorter transmembrane subunit obtained after viral protease-dependent cleavage. (b) Western blot analysis of RD114-TR envelope in three PK-7-Tat7-RD clones. Left panel, cellular extracts (40 µg/lane) were probed with the anti-RD114-TR Ab. After stripping, the membranes were hybridized with an anti-p24gag Ab to evaluate the relative proportion of RD114-TR per p24gag level. Right panel, 30 ng p24gag-equivalent of LV produced from PK-7-Tat-RD clones were processed similarly to the cellular extracts. Bracketed numbers indicate the copies of integrated SIN-RD114-TR-IN-RRE vector. (c) Western blot analysis of RD114-TR envelope in three PK-7-RD clones. Left panel, cellular extracts (40 µg/lane) were probed with the anti-RD114-TR Ab. After stripping, the membrane was hybridized with an anti-p24gag Ab. Right panel, 30 ng p24gag-equivalent of LV produced from PK-7-RD clones were processed similarly to the cell extracts. Bracketed numbers indicate the copies of integrated SIN-RD114-TR-IN-RRE vector. (d) Western blot analysis of RD114-TR envelope in three PK-7-RD26 subclones. Left panel, cellular extracts (40 µg/lane) were probed with the anti-RD114-TR Ab. After stripping, the membrane was hybridized with an anti-p24gag Ab. Right panel, 30 ng p24gag-equivalent of LV produced from PK-7-RD26 subclones were processed similarly to the cell extracts. Bracketed numbers indicate the copies of integrated SIN-RD114-TR-IN-RRE vector in the left panel, and the titer of the LV generated from the subclones after transfection of the SIN-GFP transfer vector in the right panel.
Figure 6:
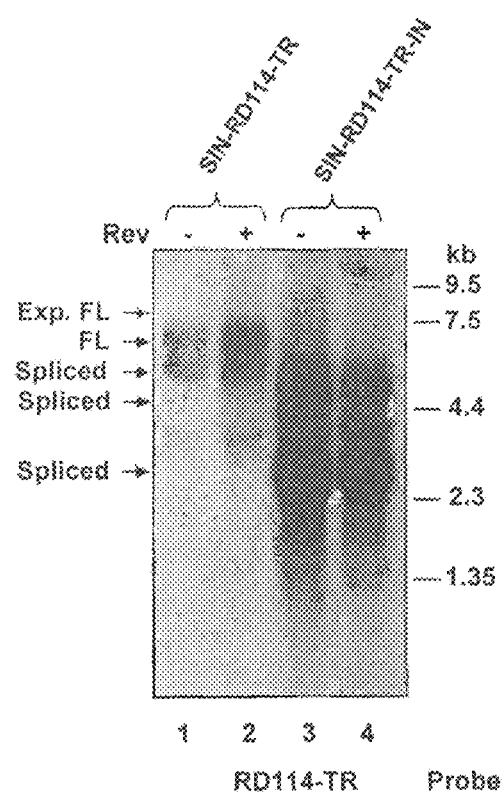
FIG. 6 Transcription of the SIN-RD114-TR and SIN-RD114-TR-IN vectors. Northern blot analysis of the expression of the RD114-TR RNA after transient transfection of the SIN-RD114-TR vectors into HEK293T cells in the presence (lanes 2 and 4) or absence (lanes 1 and 3) of extra Rev plasmid (2.5 g). Forty-eight hours after co-transfection, total RNA (5 µg) was extracted from HEK293T cells and hybridized with the specific RD114-TR probe. FL, full length; Exp. FL, expected full length of the SIN-RD114-TR-IN vector, which is expected to be 800-bp longer than the SIN-RD114-TR for the presence of the β-globin intron. A 550-bp RD114-TR fragment was used as specific probe.

To add the RD114-TR envelope into the PK-7 and PK-7-Tat7 clones by SIN-LV delivery, the first of numerous attempts consisted in the construction of the SIN-RD114-TR vector (FIG. 1a, scheme 3). To this aim, the PGK-eGFP cassette of the SIN-eGFP vector (FIG. 1a, scheme 6) was substituted with the CMV-RD114-TR cassette, which did not contain the β-globin intron present in the original CMV-RD114-TR plasmid (FIG. 1a, scheme 12). The β-globin intron was initially excluded from the construct for fear of possible multiple splicing events driven by the strong splice donor (SD) located upstream the packaging signal of the SIN vector not only with the splice acceptor (SA) located upstream the cPPT element, but also with the SA of the β-globin intron. In the latter case, in fact, the splicing would remove the CMV promoter from the genomic RNA of the vector (FIG. 1, scheme 6). Surprisingly, this SIN-vector and all intermediate plasmids with the same expression cassette configuration did not produce RD114-TR protein. In fact, when cell extracts obtained from cells transfected (TF) or transduced (TD) with the SIN-RD114-TR were analyzed by Western blot, the level of RD114-TR protein was undetectable compared to that obtained from the CMV-RD114-TR control plasmid (FIG. 4a, lanes 1-3). Northern blot analysis demonstrated that the SIN-RD114-TR-specific transcripts generated after transfection of the plasmid into PK-7 cells corresponded to the full-length (FL) and single spliced transcripts, but not to that of the internal CMV-RD114-TR cassette, suggesting the possible requirement of the β-globin intron for an efficient RD114-TR transcript accumulation (FIG. 6, lanes 1 and 2).

Based on these findings, it was argued that the unexpected requirement of the β-globin intron to obtain RD114-TR production may reflect the presence of instability or negative sequences in the RD114-TR ORF. GeneOptimizer® Assisted Sequence analysis performed by GENEART AG (Regensburg, Germany) determined that codons with a bad codon usage were spread all over the RD114-TR gene, giving reason of our assumption. Furthermore, codon optimization analysis indicated that the codon adaptation index (CAI) improved from 0.65 to 0.98 (where a CAI of 1 is the optimum). Therefore, to avoid the need of including the β-globin intron into the vector design, the entire RD114-TR ORF was codon optimized through GENEART AG service. It was found that codon optimization allowed RD114-TR PR translation even in the absence of the β-globin intron, but, unexpectedly, the high level of precursor protein (PR) was not processed by furin in the due SU and TM subunits (FIG. 4a, lanes 7). It was ruled out the possibility that accumulation of large amount of unprocessed PR was secondary to an excess of substrate because no proteolytic cleavage was documented even after very low amount of plasmid DNA transfection (10 pg DNA/10$^6$ cells). Therefore, It was concluded that one or more silent mutation(s) might have modified the rate of transcription/translation of the protein compromising therefore its correct folding and likely the accessibility of the furin-dependent cleavage.

Thus, other two vectors were generated expressing the WT RD114-TR containing the β-globin intron, the SIN-RD114-TR-IN and the SIN-RD114-TR-IN-RRE sequence (FIG. 1a, scheme 4 and 5, respectively); in the latter, an extra RRE was embedded within the β-globin intron to protect it from splicing. The SIN-RD114-TR-IN vector produced a large amount of protein after transfection (FIG. 4a, lane 6), but no protein in SIN-RD114-TR-IN transduced cells (FIG. 4a, lane 7). This finding was supported by the Northern blot analysis showing undetectable full length genomic RNA, which was expected to migrate slower than that of SIN-RD114-TR due to the presence of the 800-bp β-globin intron (FIG. 6, lanes 3 and 4, Exp. FL, full length). On the contrary, large amount of spliced RNAs derived by the action of the SD and the SA of the β-intron (FIG. 6, lane 3 and 4).

Remarkably, it was observed that the RRE in the SIN-RD114-TR-IN-RRE vector was necessary and sufficient to allow envelope expression both in transfected and transduced PK-7 cells (FIG. 4a, lanes 8 and 9) and in the respective VLPs (FIG. 4a, lanes 10 and 11). The RD114-TR incorporated into VLP was normally processed, showing high level of the trans-membrane subunits TM and TM*; the latter resulting from the cleavage of the TM subunit by the viral protease, as shown by Sandrin et al., 2004 [22]. The RD114-TR SU subunit, which should co-migrate with the PR molecule is not detected by the specific anti-RD114-TR we used. Next, we generated a SIN-RD114-TR-CO-IN-RRE vector and tested for protein production and processing. Yet, no protein produced from this vector was properly produced and processed (FIG. 4a, lane 13). This result leads to conclude that the only available construct for the correct production of RD114-TR is the SIN-RD114-TR-IN-RRE.

Example V: Development of the PK-7-Tat7-RD19 Clone to Obtain RD2-MolPack and of the PK-7-RD32 Clone to Obtain RD3-MolPack Based on the results presented so far, the RD114-TR envelope was stably integrated into both the PK-7-Tat7 and PK-7 clones by VSV-G pseudotyped SIN-RD114-TR-IN-RRE LV delivery. PK-7-Tat7 cells were spinoculated and cloned by limiting dilution. Next, nine clones were screened by calculating the titer of LV produced after transduction of the $2^{nd}$ generation PΔN-eGFP transfer vector (Table 4); the level of RD114-TR was controlled by Western blot and the number of integrated copies by TaqMan PCR only on those clones showing a titer $\geq 1\times 10^5$ TU/ml, that is PK-7-Tat7-RD3, PK-7-Tat7-RD12, and PK-7-Tat7-RD19 clones (FIG. 4b). PK-7-Tat7-RD19 clone was chosen because it produced the highest titer and a good amount of RD114-TR in relation to the number of SIN-RD114-TR-IN-RRE LV integrated copies (FIG. 4b, bracketed numbers).

TABLE 4

Potency of LV produced from PK-7-Tat7-RD clones

| Clones | Titer (TU/ml)[a] |
|---|---|
| PK-7-TBt7-RD3 | $1.0 \times 10^6$ |
| PK-7-Tat7-RD12 | $1.4 \times 10^5$ |
| PK-7-Tat7-RD19 | $\mathbf{3.0 \times 10^5}$ |
| PK-7 | $2.4 \times 10^4$ |
| HEK-293T | $1.5 \times 10^3$ |
| | p24Gag (ng/ml) |
| PK-7-Tat7-RD3 | 56 |
| PK-7-Tat7-RD12 | 121 |
| PK-7-Tat7-RD19 | 10 |
| PK-7 | 99 |
| HEK-293T | 122 |
| | Infectivity (TU/ng p24Gag) |
| PK-7-Tat7-RD3 | $1.7 \times 10^3$ |
| PK-7-Tat7-RD12 | $1.1 \times 10^3$ |
| PK-7-Tat7-RD19 | $\mathbf{3.0 \times 10^4}$ |
| PK-7 | $2.4 \times 10^2$ |
| HEK-293T | $0.1 \times 10^2$ |

[a]Titer of LVs produced after transduction of PK-7-Tat7-RD clones with PΔN-eGFP vector. PK-7 cells were transfected with the CMV-RD114-TR and PΔN-eGFP plasmids, whereas HEK-293T cells with the CMV-RD114-TR, CMV-GPRT and PΔN-eGFP plasmids.

Next, the same transduction, selection, cloning and screening protocols adopted to generate PK-7-Tat7-RD clones, were followed also to integrate RD114-TR into PK-7 cells (Table 5). The chosen PK-7-RD-26, PK-7-RD-28 and PK-7-RD-32 cells were tested by Western blot and TaqMan PCR techniques (FIG. 4c). It was opted for PK-7-RD26 clone because, despite the fact that it produces LV with low titer, it produces the highest level of p24gag compared to the other selected clones and even compared to the progenitor PK-7 clone (Table 7).

TABLE 5

Potency of LV produced from PK-7-RD selected clones

| | SupT1 | CD34+ |
|---|---|---|
| | Titer (TU/ml)[a] | |
| PK-7-RD26 | $7.5 \times 10^4$ | $2.0 \times 10^5$ |
| PK-7-RD28 | $1.4 \times 10^4$ | $1.0 \times 10^5$ |
| PK-7-RD32 | $2.7 \times 10^4$ | $1.7 \times 10^5$ |

TABLE 5-continued

Potency of LV produced from PK-7-RD selected clones

| | SupT1 | CD34+ |
|---|---|---|
| PK-7 | $3.3 \times 10^4$ | $3.6 \times 10^3$ |
| HEK-293T | $1.2 \times 10^5$ | $1.6 \times 10^5$ |
| | p24Gag (ng/ml) | |
| PK-7-RD26 | 127 | |
| PK-7-RD28 | 34 | |
| PK-7-RD32 | 53 | |
| PK-7 | 38 | |
| HEK-293T | 135 | |
| | Infectivity (TU/ng p24Gag) | |
| PK-7-RD26 | $\mathbf{6.0 \times 10^2}$ | $\mathbf{1.5 \times 10^3}$ |
| PK-7-RD28 | $4.0 \times 10^2$ | $2.9 \times 10^3$ |
| PK-7-RD32 | $5.0 \times 10^2$ | $3.0 \times 10^3$ |
| PK-7 | $8.7 \times 10^2$ | $1.0 \times 10^2$ |
| HEK-293T | $8.8 \times 10^2$ | $1.1 \times 10^3$ |

[a]Titer of LVs produced after transfection of PK-7-RD clones with SIN-GFP plasmid, of PK-7 clone with SIN-GFP and RD114-TR plasmids and of HEK-293T with CMV-GPR, SIN-GFP and RD114-TR plasmids, respectively.

Of interest, the level of RD114-TR™ subunit was equivalent in PK-7-RD28 and PK-7-RD32 clones in the face of a conspicuous difference in the number of RD114-TR copies between the two (FIG. 4c, bracketed numbers), suggesting that part of the SIN-RD114-TR-IN-RRE vectors must be not functional in PK-7-RD32 clone. Thus, to combine the high level of p24gag production and a possibly higher level of RD114-TR protein in the PK-7-RD26 clone other two cycles of SIN-RD114-TR-IN-RRE integration, selection and cloning were carried out obtaining from the first cycle the subclone PK-7-RD26.72, and from the second cycle the subclone RD26.72.10, increasing the number of RD114-TR copies from 2 to 11 and then 22, and the titer from $7.0\times 10^2$ to $1.1\times 10^4$ and to finally $2.7\times 10^5$, respectively (FIG. 4d, bracketed numbers).

Example VI: Development of the $2^{nd}$ Generation RD-MolPack-Chim3 Stable Producer Cell Line To obtain the final $2^{nd}$ generation RD-MolPack packaging cells, it was integrated into the PK-7-Tat7-RD19 cells the transfer vector PΔN-Chim3 (FIG. 1a, scheme 7), whose therapeutic gene Chim3 has been extensively characterized in the context of anti-HIV/AIDS gene therapy [23,24]. After the standardized screening protocol, the three clones PK-7-Tat7-RD19-Chim3.2, PK-7-Tat7-RD19-Chim3.3 and PK-7-Tat7-RD19-Chim3.14 (Table 6) were chose for further characterization.

TABLE 6

Potency of LV produced from RD2-MolPack-Chim3 clones

| Clones | SupT1 | CD34 |
|---|---|---|
| | Titer (TU/ml) | |
| RD2-MolPack-Chim3.2 | $2.6 \times 10^5$ | $1.1 \times 10^5$ |
| RD2-MolPack-Chim3.3 | $3.9 \times 10^5$ | $2.6 \times 10^5$ |
| RD2-MolPack-Chim3.14[a] | $\mathbf{0.3 - 1 \times 10^6}$ | $5.1 \times 10^5$ |
| PK-7[b] | $1.3 \times 10^5$ | $1.5 \times 10^5$ |
| HEK-293T[c] | $6.5 \times 10^3$ | $5.1 \times 10^5$ |
| | p24Gag (ng/ml) | |
| RD2-MolPack-Chim3.2[b] | 74 | 112 |
| RD2-MolPack-Chim3.3 | 40 | 120 |
| RD2-MolPack-Chim3.14[b] | 127 | 101 |

TABLE 6-continued

Potency of LV produced from RD2-MolPack-Chim3 clones

| Clones | SupT1 | CD34 |
|---|---|---|
| PK-7 | 102 | 88 |
| HEK-293T | 437 | 493 |
| | Infectivity (TU/ng p24Gag) | |
| RD2-MolPack-Chim3.2[b] | $3.5 \times 10^3$ | $9.0 \times 10^2$ |
| RD2-MolPack-Chim3.3 | $9.0 \times 10^3$ | $2.2 \times 10^3$ |
| RD2-MolPack-Chim3.14[b] | $\mathbf{5.2 - 8 \times 10^3}$ | $\mathbf{5.0 \times 10^3}$ |
| PK-7 | $1.6 \times 10^2$ | $1.7 \times 10^3$ |
| HEK-293T | $0.8 \times 10^2$ | $0.1 \times 10^2$ |

[a]Bold indicates the selected clone.
[b]LV were produced after transfection of PK-7 cells with the PΔN-Chim3 transfer vector and RD114-TR envelope plasmids.
[c]LV were produced after transfection of HEK-293Tcells with CMV-GPR, PΔN-Chim3 transfer vector and RD114-TR envelope plasmids.
LV were tested on target cells 3 days after transduction.

It was selected the PK-7-Tat7-RD19-Chim3.14 clone (hereafter RD2-MolPack-Chim3.14) because it spontaneously grows in suspension. It was verified that the clone survives in culture for close to two months generating 3TU/cell/day when the titer was determined on SupT1 cells. Furthermore, RD2-MolPack-Chim3.14 cells can normally survive in DMEM medium containing 5% FCS, whereas its viability decreases when it is adapted to growth in DMEM medium containing 2.5% FCS (FIG. 3d). Its growing features are important for the potential large-scale cultivation in a bioreactor. It was also verified that despite the high copy number of the integrated Chim3-LV, no rearrangement of the viral genes was observed by means of Southern blot analysis, proving genetic stability of the integrated vectors (FIG. 3c). Strikingly, the titer of the LV produced from RD2-MolPack-Chim3.14 clone is higher than that of LV produced from transiently transfected PK-7 and HEK293T control cells with the remaining plasmids when calculated either on SupT1 or CD34+ cells (Table 6).

REFERENCES

1. Schambach, A., and Baum, C. (2008). Clinical application of lentiviral vectors—concepts and practice. *Curr Gene Ther* 8: 474-482.
2. Carroll, R., Lin, J. T., Dacquel, E. J., Mosca, J. D., Burke, D. S., and St Louis, D. C. (1994). A human immunodeficiency virus type 1 (HIV-1)-based retroviral vector system utilizing stable HIV-1 packaging cell lines. *J Virol* 68: 6047-6051.
3. Yu, H., Rabson, A. B., Kaul, M., Ron, Y., and Dougherty, J. P. (1996). Inducible human immunodeficiency virus type 1 packaging cell lines. *J Virol* 70: 4530-4537.
4. Poeschla, E., Corbeau, P., and Wong-Staal, F. (1996). Development of HIV vectors for anti-HIV gene therapy. *Proc Natl Acad Sci USA* 93: 11395-11399.
5. Corbeau, P., Kraus, G., and Wong-Staal, F. (1996). Efficient gene transfer by a human immunodeficiency virus type 1 (HIV-1)-derived vector utilizing a stable HIV packaging cell line. *Proc Natl Acad Sci USA* 93: 14070-14075.
6. Throm, R. E., et al. (2009). Efficient construction of producer cell lines for a SIN lentiviral vector for SCID-X1 gene therapy by concatemeric array transfection. *Blood* 113: 5104-5110.
7. Broussau, S., et al. (2008). Inducible packaging cells for large-scale production of lentiviral vectors in serum-free suspension culture. *Mol Ther* 16: 500-507.
8. Srinivasakumar, N., Chazal, N., Helga-Maria, C., Prasad, S., Hammarskjold, M. L., and Rekosh, D. (1997). The effect of viral regulatory protein expression on gene delivery by human immunodeficiency virus type 1 vectors produced in stable packaging cell lines. *J Virol* 71: 5841-5848.
9. Kaul, M., Yu, H., Ron, Y., and Dougherty, J. P. (1998). Regulated lentiviral packaging cell line devoid of most viral cis-acting sequences. *Virology* 249: 167-174.
10. Cockrell, A. S., Ma, H., Fu, K., McCown, T. J., and Kafri, T. (2006). A trans-lentiviral packaging cell line for high-titer conditional self-inactivating HIV-1 vectors. *Mol Ther* 14: 276-284.
11. Bestor, T. H. (2000). Gene silencing as a threat to the success of gene therapy. *J Clin Invest* 105: 409-411.
12. Ikeda, Y., Takeuchi, Y., Martin, F., Cosset, F. L., Mitrophanous, K., and Collins, M. (2003). Continuous high-titer HIV-1 vector production. *Nat Biotechnol* 21: 569-572.
13. Palombo, F., Monciotti, A., Recchia, A., Cortese, R., Ciliberto, G., and La Monica, N. (1998). Site-specific integration in mammalian cells mediated by a new hybrid baculovirus-adeno-associated virus vector. *J. Virol.* 72: 5025-5034.
14. Smith, R. H. (2008). Adeno-associated virus integration: virus versus vector. *Gene Ther* 15: 817-822.
15. Sandrin, V., et al. (2002). Lentiviral vectors pseudotyped with a modified RD114 envelope glycoprotein show increased stability in sera and augmented transduction of primary lymphocytes and CD34+ cells derived from human and nonhuman primates. *Blood* 100: 823-832.
16. Berns, K. I., and Linden, R. M. (1975). The cryptic lyfe style of adeno-associated virus. *Bioessays* 17: 237-245.
17. Cheung, A. K., Hoggan, M. D., Hauswirth, W. W., and Berns, K. I. (1980). Integration of the adeno-associated virus genome into cellular DNA in latently infected human Detroit 6 cells. *J Virol* 33: 739-748.
18. Samulski, R. J., Chang, L. S., and Shenk, T. (1987). A recombinant plasmid from which an infectious adeno-associated virus genome can be excised in vitro and its use to study viral replication. *J Virol* 61: 3096-3101.
19. Recchia, A., Perani, L., Sartori, D., Olgiati, C., and Mavilio, F. (2004). Site-specific integration of functional transgenes into the human genome by adeno/AAV hybrid vectors. *Mol Ther* 10: 660-670.
20. Zufferey, R., Nagy, D., Mandel, R. J., Naldini, L., and Trono, D. (1997). Multiply attenuated lentiviral vector achieves efficient gene delivery in vivo. *Nat Biotechnol* 15: 871-875.
21. Follenzi, A., Ailles, L. E., Bakovic, S., Geuna, M., and Naldini, L. (2000). Gene transfer by lentiviral vectors is limited by nuclear translocation and rescued by HIV-1 pol sequences. *Nat Genet* 25: 217-222.
22. Sandrin, V., Muriaux, D., Darlix, J. L., and Cosset, F. L. (2004). Intracellular trafficking of Gag and Env proteins and their interactions modulate pseudotyping of retroviruses. *J Virol* 78: 7153-7164.
23. Porcellini, S., et al. (2009). The F12-Vif derivative Chim3 inhibits HIV-1 replication in CD4+T lymphocytes and CD34+-derived macrophages by blocking HIV-1 DNA integration. *Blood* 113: 3443-3452.
24. Porcellini, S., Gubinelli, F., Alberici, L., Piovani, B. M., Rizzardi, G. P., and Bovolenta, C. (2010). Chim3 confers survival advantage to CD4+ T cells upon HIV-1 infection by preventing HIV-1 DNA integration and HIV-1-induced G2 cell-cycle delay. *Blood* 115: 4021-4029.

25. Zufferey, R., Nagy, D., Mandel, R. J., Naldini, L., and Trono, D. (1997). Multiply attenuated lentiviral vector achieves efficient gene delivery in vivo. *Nat Biotechnol* 15: 871-875.
26. Di Nunzio, F., Piovani, B., Cosset, F. L., Mavilio, F., and Stornaiuolo, A. (2007). Transduction of human hematopoietic stem cells by lentiviral vectors pseudotyped with the RD114-TR chimeric envelope glycoprotein. *Hum Gene Ther* 18: 811-820.
27. Dull, T., Zufferey, R., Kelly, M., Mandel, R. J., Nguyen, M., Trono, D., Naldini, L. A third-generation lentivirus vector with a conditional packaging system. J Virol, 1998; 72: 8463-71

The invention claimed is:

1. A method for producing lentiviral vectors comprising:
   i) culturing a stable mammalian lentiviral packaging cell line, wherein the cell line comprises at least one copy of an integration cassette stably integrated into its genome and at least one copy of an env gene, wherein the at least one integration cassette comprises:
      (a) adeno-associated virus (AAV) inverted terminal repeats (ITRs) flanking the integration cassette, and
      (b) a first expression cassette and a second expression cassette, wherein the first expression cassette encodes lentiviral gag and pol and the second expression cassette encodes lentiviral rev and a selection marker;
   ii) inserting a transfer vector into the cell line;
   iii) obtaining a producer cell line expressing env, lentiviral gag, lentiviral pol, lentiviral rev, and the selection marker; and
   iv) obtaining the lentiviral vectors from the producer cell line.

2. The method according to claim 1, wherein the cell line further comprises a human immunodeficiency virus-1 (HIV-1) tat gene stably integrated into its genome.

3. The method according to claim 1, wherein the cell line originated from a human cell line selected from the group consisting of: HEK293, HEK293-T, HEK293-SF, TE671, HT1080, and HeLa.

4. The method according to claim 1, wherein the first and second expression cassettes of the integration cassette are tail-to-tail oriented and each one is flanked by a constitutive promoter and a poly A tail.

5. The method according to claim 4, wherein the promoter is selected from the group consisting of: CMV promoter, CMV IE promoter, PGK promoter, SV40 promoter, eF1α promoter, SFFV promoter, and RSV promoter.

6. The method according to claim 1, wherein the selection marker is selected from the group consisting of: hygromycin, kanamycin, neomycin, and zeomycin resistance genes.

7. The method according to claim 1, wherein the env gene is selected from the group consisting of: MLV 4070 env, RD114 env, chimeric envelope protein RD114-TR, chimeric envelope protein RD114-pro, baculovirus GP64 env, and GALV env.

8. The method according to claim 1, wherein the env gene is the gene encoding the chimeric envelope protein RD114-TR.

* * * * *